United States Patent [19]

Konishi et al.

[11] Patent Number: 4,565,569

[45] Date of Patent: * Jan. 21, 1986

[54] DIPHENYL SULFONE COMPOUNDS, AND THEIR PRODUCTION AND USE

[75] Inventors: Hiroyuki Konishi, Sakai; Naganori Hino; Hiroshi Matsumoto, both of Toyonaka; Ryo Yoshida, Kawanishi, all of Japan

[73] Assignee: Sumitomo Chemical Company, Limited, Osaka, Japan

[*] Notice: The portion of the term of this patent subsequent to Feb. 22, 2000 has been disclaimed.

[21] Appl. No.: 494,453

[22] Filed: May 13, 1983

Related U.S. Application Data

[63] Continuation-in-part of Ser. No. 441,381, Nov. 12, 1982.

[30] Foreign Application Priority Data

May 14, 1982 [JP] Japan ................................. 57-81750
Aug. 6, 1982 [JP] Japan ................................. 57-137790

[51] Int. Cl.⁴ ..................... B21H 3/04; C07C 147/107; C07C 121/50
[52] U.S. Cl. ......................................... 71/103; 568/33; 560/11; 260/465 D; 260/465 F; 549/504
[58] Field of Search ......... 71/103; 260/465 D, 465 F; 568/33; 560/11; 549/504

[56] References Cited

U.S. PATENT DOCUMENTS 3,426,075  2/1969  Campbell .
3,957,865  5/1976  Rohe et al. .
4,335,249  6/1982  Johnson et al. .
4,374,662  2/1983  Konishi et al. ........................ 71/103

FOREIGN PATENT DOCUMENTS 8107462  10/1982  Brazil .

OTHER PUBLICATIONS

Chemical Abstracts, 56, 8612i (1962).
Chemical Abstracts, 82, 150504z (1957).

Primary Examiner—Delbert R. Phillips

Attorney, Agent, or Firm—Birch, Stewart, Kolasch & Birch

[57] ABSTRACT

A diphenyl sulfone compound of the formula:

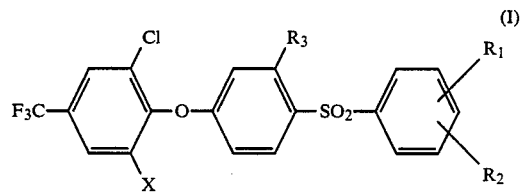

wherein $R_1$ and $R_2$ are, same or different, each a hydrogen atom, a halogen atom, a lower alkyl group, a lower alkoxy group, a lower alkenyloxy group, a lower alkynyloxy group, a phenoxy group, a lower alkylthio group, a lower alkylsulfonyl group or a lower alkoxycarbonyl(lower)alkoxy group, $R_3$ is a hydroxyl group, a lower alkenyloxy group, a lower alkynyloxy group, a halo(lower)alkoxy group, a dihalo(lower)alkoxy group, a lower alkoxy(lower)alkoxy group, a cyano(lower)alkoxy group, a lower alkoxycyano(lower)alkoxy group, a hydroxy(lower)alkoxy group, a lower alkylcarbonyloxy group, a lower alkoxycarbonyl group, a lower alkylthio(lower)alkoxy group, a lower alkenyloxy(lower)alkoxy group, a di(lower)alkylamino(lower)alkoxy group, a hydroxyimino(lower)alkoxy group, a lower alkoxyimino(lower)alkoxy group, a lower alkylsulfonyloxy group, a lower alkoxycarbonyloxy group, a di(lower)alkoxyphosphinyloxy group, an oxotetrahydrofuranyloxy group, a tetrahydropyranyloxy group, a lower alkyl-1,3-oxolanyl(lower)alkoxy group or a group of the formula: —O—A—COR₄ (in which A is lower alkylene, lower alkenylene, lower alkyleneoxy, halo(lower)alkylene or lower alkoxy(lower)alkylene and $R_4$ is hydroxyl, lower alkyl, halo(lower)alkyl, lower alkoxy, lower alkenyloxy, lower alkynyloxy, halo(lower)alkoxy, lower alkoxy(lower)alkoxy, cyano(lower)alkoxy, lower alkoxycarbonyl(lower)alkoxy, di(lower)alkylamino, N-(α-lower alkyl(lower)alkylidene)aminoxy or lower alkylthio) and X is a hydrogen atom or a halogen atom, which is useful as a herbicide.

17 Claims, No Drawings

DIPHENYL SULFONE COMPOUNDS, AND THEIR PRODUCTION AND USE

This is a continuation-in-part application of our co-pending Application Ser. No. 441,381 filed Nov. 12, 1982.

The present invention relates to diphenyl sulfone compounds, and their production and use. More particularly, it relates to novel diphenyl sulfone compounds represented by the formula:

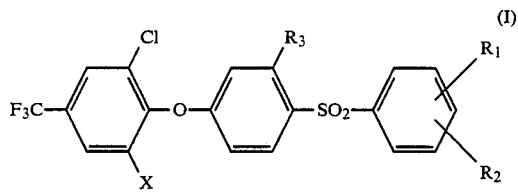

wherein $R_1$ and $R_2$ are, same or different, each a hydrogen atom, a halogen atom, a lower alkyl group, a lower alkoxy group, a lower alkenyloxy group, a lower alkynyloxy group, a phenoxy group, a lower alkylthio group, a lower alkylsulfonyl group or a lower alkoxycarbonyl(lower)alkoxy group, $R_3$ is a hydroxyl group, a lower alkenyloxy group, a lower alkynyloxy group, a halo(lower)alkoxy group, a dihalo(lower)alkoxy group, a lower alkoxy(lower)alkoxy group, a cyano(lower)alkoxy group, a lower alkoxycyano(lower)alkoxy group, a hydroxy(lower)alkoxy group, a lower alkylcarbonyloxy group, a lower alkoxycarbonyl group, a lower alkylthio(lower)alkoxy group, a lower alkenyloxy(lower)alkoxy group, a di(lower)alkylamino(lower)alkoxy group, a hydroxyimino(lower)alkoxy group, a lower alkoxyimino(lower)alkoxy group, a lower alkylsulfonyloxy group, a lower alkoxycarbonyloxy group, a di(lower)alkoxyphosphinyloxy group, an oxotetrahydrofuranyloxy group, a tetrahydropyranyloxy group, a lower alkyl-1,3-oxolanyl(lower)alkoxy group or a group of the formula: —O—A—COR$_4$ (in which A is lower alkylene, lower alkenylene, lower alkyleneoxy, halo(lower)alkylene or lower alkoxy(lower)alkylene and R$_4$ is hydroxyl, lower alkyl, halo(lower)alkyl, lower alkoxy, lower alkenyloxy, lower alkynyloxy, halo(lower)alkoxy, lower alkoxy(lower)alkoxy, cyano(lower)alkoxy, lower alkoxycarbonyl(lower)alkoxy, di(lower)alkylamino, N-(α-lower alkyl(lower)alkylidene)aminoxy or lower alkylthio) and X is a hydrogen atom or a halogen atom, and their production and their use as herbicides.

In the above significances, the term "lower" is intended to mean any group having not more than 5 carbon atoms, and the term "halogen" may include chlorine, bromine, fluorine and iodine.

Among various diphenyl sulfone compounds, preferred are those of the formula (I) wherein $R_1$ and $R_2$ are, same or different, each hydrogen, fluorine, chlorine, bromine, $C_1$-$C_2$ alkyl, $C_1$-$C_2$ alkoxy, propenyloxy, propynyloxy, phenoxy, methylthio, methylsulfonyl or $C_1$-$C_2$ alkoxycarbonyl($C_1$-$C_2$)alkoxy, $R_3$ is hydroxyl, propenyloxy, propynyloxy, chloroethoxy, difluoromethoxy, $C_1$-$C_2$ alkoxy($C_1$-$C_2$)alkoxy, cyanomethoxy, cyanomethoxymethoxy, hydroxyethoxy, ethoxycarbonyl, $C_1$-$C_2$ alkylthio($C_1$-$C_2$)alkoxy, ethenyloxyethoxy, N,N-di($C_1$-$C_2$) alkylaminoethoxy, hydroxyiminoethoxy, methoxyiminoethoxy, methylsulfonyloxy, methoxycarbonyloxy, diethoxyphosphinyloxy, oxotetrahydrofuranyloxy, tetrahydropyranyloxy, methyl-1,3-oxolanyl($C_1$-$C_2$)alkoxy or methylcarbonyloxy, A is $C_1$-$C_2$ alkylene, propenylene, ethyleneoxy, fluoromethylene or methoxymethylene and R$_4$ is $C_1$-$C_4$ alkyl, chloromethyl, hydroxyl, $C_1$-$C_5$ alkoxy, chloroethoxy, propenyloxy, ethoxycarbonylethoxy, α-methylethylideneaminoxy, N,N-dimethylamino, cyanomethoxy, methoxyethoxy, ethylthio or propynyloxy. More preferred are those of the formula (I) wherein $R_1$ and $R_2$ are, same or different, each hydrogen, methyl, ethyl, fluorine, chlorine, bromine, methoxy or ethoxy, $R_3$ is chloroethoxy, methoxymethoxy, cyanomethoxy, methoxycyanomethoxy, hydroxyethoxy, methylcarbonylmethoxy, α-(methylcarbonyl)ethoxy, methylthiomethoxy, methoxyiminopropoxy, diethoxyphosphinyloxy, oxotetrahydrofuranyloxy, methoxycarbonylmethoxy, ethoxycarbonylmethoxy, α-(methoxycarbonyl)ethoxy, methoxy(methoxycarbonyl)methoxy, α-(ethoxycarbonyl)ethoxy, ethylthiocarbonylmethoxy, propinyloxycarbonylmethoxy, 2-methyl-1,3-oxolan-2-ylmethoxy, α-(2-methyl-1,3-oxolan-2-yl)ethoxy, β-(methylcarbonyloxy)ethoxy, β-(ethoxycarbonyloxy)ethoxy or dimethylaminocarbonylmethoxy and X is hydrogen or chlorine. Specific examples of the preferred diphenyl sulfone compounds (I) are as follows: 4-(2-chloro-4-trifluoromethylphenoxy)-2-cyanomethoxy-4'-methyl-diphenyl sulfone, 4-(2-chloro-4-trifluoromethylphenoxy)-2-cyanomethoxy-4'-chlorodiphenyl sulfone, 4-(2-chloro-4-trifluoromethylphenoxy)-2-methoxycarbonylmethoxydiphenyl sulfone, 4-(2-chloro-4-trifluoromethylphenoxy)-2-methoxycarbonylmethoxy-4'-methyl-diphenyl sulfone, 4-(2-chloro-4-trifluoromethylphenoxy)-2-methoxycarbonylmethoxy-4'-chlorodiphenyl sulfone, 4-(2-chloro-4-trifluoromethylphenoxy)-2-ethoxycarbonylmethoxy-4'-methyldiphenyl sulfone, 4-(2-chloro-4-trifluoromethylphenoxy)-2-methoxycarbonylmethoxy-4'-fluorodiphenyl sulfone, 4-(2-chloro-4-trifluoromethylphenoxy)-2-methoxy(methoxycarbonyl)-methoxydiphenyl sulfone, 4-(2-chloro-4-trifluoromethylphenoxy)-2-[methoxy(methoxycarbonyl)methoxy]-4'-chlorodiphenyl sulfone, 4-(2-chloro-4-trifluoromethylphenoxy)-2-(1-acetylethoxy)-4-chlorodiphenyl sulfone, 4-(2-chloro-4-trifluoromethylphenoxy)-2-(1-acetylethoxy)-4'-fluorodiphenyl sulfone, etc.

Generally, herbicides are required to be so effective as can exterminate a great deal of weeds unfavorably grown in paddy rice field, crop field, orchards, etc. Further, it is desirous that herbicides show a prominent herbicidal activity against a wide variety of weeds causing no or lesser damage on important crop plants. The use of herbicides in a large dose can occasionally attain a high preventive effect; however, it results in increase of the phytotoxicity to crop plants and thus decrease of the crop yield. Moreover, the environmental pollution due to agricultural chemicals is nowadays a great social problem, and therefore herbicides are desired to produce a significant herbicidal effect in a small dose and yet to be less residual.

As a result of the extensive study, its has now been found that the diphenyl sulfone compounds (I) show a strong herbicical activity against a wide variety of weeds including broad-leaved weeds such as radish (*Raphanus sativus*), velvetleaf (*Abutilon theophrasti*), sunflower (*Helianthus annuus*), Cocklebur (*Xanthium pennsylvanicum*), tall morningglory (*Ipomoea purpurea*), hemp sesbania (Sesbania sp.), redroot pigweed (*Amaranthus retroflexus*), birdseye speedwell (*Veronica persica), black nightshade (*Solanum nigrum*), prickly sida (*Sida spinosa*), pineappleweed (Matricaria spp.) and wild buckwheat (*Polygonum convolvulus*) and Graminaceous weeds such as barnyardgrass (*Echinochloa crusgalli*) and wide oat (*Avena fatua*) in crop field by pre-emergence or post-emergence treatment. They are also effective in preventing the growth of Graminaceous weeds such as barnyardgrass, broad-leaved weeds such as false pimpernel (*Lindernia procumbens*), toothcup (*Rotala indica*), waterwort (*Elatine triandra*), *Vandelcia angustifolia* and *Dopatrium junceum*, Cyperaceae weeds such as nutsedge (*Cyperus difformis*), hardstem bulrush (*Scirpus juncoides*) and slender spikerush (*Eleocharis acicularis*), monochoria (*Monochoria vaginalis*), arrowhead (*Sagittaria pygmaea*), etc. in paddy rice field by pre-emergence or post-emergence treatment.

Advantageously, the diphenyl sulfone compounds (I) do not exert any material toxicity to important crop plants such as corn, wheat, soybean, cotton and rice plant. They exert a high herbicidal activity when applied to crop field by post-emergence foliar treatment, although a herbicidal activity can be also exerted by pre-emergence treatment. In case of post emergence foliar treatment, such broad-leaved weeds as radish, velvetleat, sunflower, cocklebur, tall morningglory, hemp sesbania, redroot pigweed, birdseye speedwell and black nightshade can be exterminated. Their herbicidal activity extent to the Graminaceous weeds such as barnyardgrass and wild oat as well. Besides, the diphenyl sulfone compounds (I) have a high selectivity, in addition to their strong herbicidal activity, over the important crop plants and the harmful weeds germinated in the field of such crop plants so that it becomes possible to control the germination of weeds without causing any toxicity to the crop plants. For instance, sunflower, cocklebur, tall morningglory, hemp sesbania, velvetleaf, redroot pigweed, etc. in the field of corn or soybean can be controlled by an approximate choice of the dosage while giving no injury to corn or soybean. Likewise, radish, birdseye speedwell, black nightshade, etc. in the field of wheat can be controlled without causing any toxicity to wheat.

In the pre-emergence treament, the diphenyl sulfone compounds (I) produce a high herbicidal activity on broad-leaved weeds while showing a selectivity to crop plants such as soybean, cotton, wheat and corn. The germination of harmful weeds such as barnyardgrass, false pimpernel, toothcup, hardstem bulrush and arrowhead in the paddy rice field is effectively prevented. Accordingly, the diphenyl sulfone compounds (I) can be used as herbicides applicable to paddy field as well as agricultural plowed field. They are also useful as herbicides to be employed for orchard, non-agricultural field, forest, etc.

The diphenyl sulfone compounds (I) can be produced by various procedures, among which typical examples are shown below:

Procedure A

The diphenyl sulfone compounds of the formula:

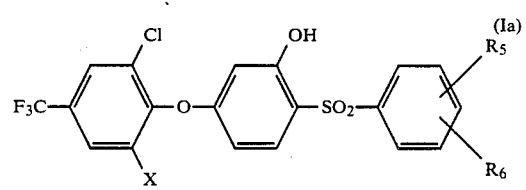

wherein $R_5$ and $R_6$ are, same or different, each a hydrogen atom, a halogen atom, a lower alkyl group, a lower alkoxy group, a phenoxy group, a lower alkylthio group or a lower alkylsulfonyl group and X is as defined above can be produced by reacting a compound of the formula:

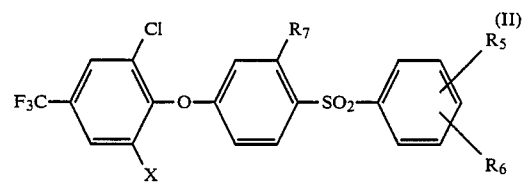

wherein $R_7$ is a lower alkoxy group and $R_5$, $R_6$ and X are each as defined above, with an ether linkage cleaving agent in an inert solvent.

As the ether linkage cleaving agent, there may be used a Lewis acid (e.g. boron tribromide, boron triiodide, ferric chloride, zinc chloride), a mineral acid (e.g. hydrochloric acid, hydrobromic acid, hydroiodic acid), etc. Examples of the inert solvent are aromatic hydrocarbons (e.g. benzene, toluene, xylene), chlorinated hydrocarbons (e.g. chloroform, carbon tetrachloride, dichloromethane, 1,2-dichloroethane, chlorobenzene, dichlorobenzene), formic acid, acetic acid, nitroethane, nitrobenzene, water, etc. The amount of the ether linkage cleaving agent may be normally from 0.9 to 10 equivalents to the starting compound (II). The reaction is usually carried out at a temperature of −50° to 150° C., preferably of 1° to 120° C.

Procedure B

The diphenyl sulfone compounds of the formula:

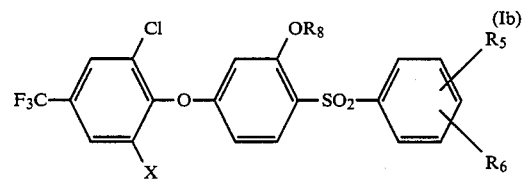

wherein $R_8$ is a lower alkenyl group, a lower alkynyl group, a halo(lower)alkyl group, a lower alkoxy(lower)alkyl group, a cyano(lower)alkyl group, a lower alkoxycyano(lower)alkyl group, a hydroxy(lower)alkyl group, a lower alkylcarbonyloxy(lower)alkyl group, a lower alkylthio(lower)alkyl group, a lower alkenyloxy(lower)alkyl group, a di(lower)alkylamino(lower)alkyl group, a hydroxyimino(lower)alkyl group, a lower alkoxyimino(lower)alkyl group, a lower alkylsulfonyl group, a lower alkoxycarbonyl group, a di(lower)alkoxyphosphinyl group, an oxotetrahydrofuranyl group, a tetrahydropyranyl group, a lower alkyl-1,3-oxolanyl(lower)alkyl group or a group of the formula: —A—COR₄ (wherein A and $R_4$ are each as defined above)

and $R_5$, $R_6$ and X are each as defined above can be produced by reacting the compound (Ia) with a halide of the formula:

$$R_8-Y$$

wherein Y is a halogen atom and $R_8$ is as defined above in an inert solvent in the presence of a hydrogen halide-eliminating agent.

Examples of the inert solvent are benzene, toluene, xylene, dimethylformamide, dimethylsulfoxide, methanol, ethanol, acetone, methylethylketone, etc. As the hydrogen halide-eliminating agent, there may be exemplified pyridine, triethylamine, N,N-dimethylaniline, N,N-diethylaniline, sodium carbonate, potassium carbonate, sodium hydrogen carbonate, sodium hydride, sodium hydroxide, potassium hydroxide, sodium methoxide, potassium ethoxide, etc. The halide and the hydrogen halide-eliminating agent may be employed respectively in an amount of 0.9 to 2 equivalents to the starting compound (Ia). The reaction is normally effected at a temperature of 0° to 150° C., preferably of 20° to 100° C.

Procedure C

The diphenyl sulfone compounds of the formula:

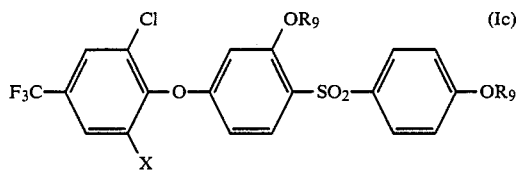

wherein $R_9$ is a lower alkenyl group, a lower alkynyl group or a lower alkoxycarbonyl(lower)alkyl group and X is as defined above can be produced from a compound of the formula:

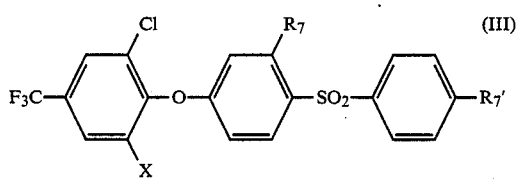

wherein $R_7$ and $R_7'$ are each a lower alkoxy group and X is as defined above by reacting the latter with an ether linkage cleaving agent in an inert solvent and reacting the resultant compound of the formula:

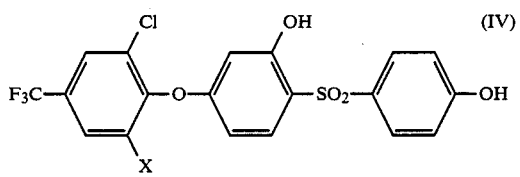

wherein Z is as defined above with a halide of the formula:

$$R_9-Z$$

wherein Z is a halogen atom and $R_9$ is as defined above in an inert solvent in the presence of a hydrogen halide-eliminating agent.

In the former step, there may be used as the ether linkage cleaving agent a Lewis acid (e.g. boron tribromide, boron triiodide, ferric chloride, zinc chloride), a mineral acid (e.g. hydrochloric acid, hydrobromic acid, hydroiodic acid) or the like. Examples of the inert solvent are aromatic hydrocarbons (e.g. benzene, toluene, xylene), chlorinated hydrocarbons (e.g. chloroform, carbon tetrachloride, dichloromethane, 1,2-dichloroethane, chlorobenzene, dichlorobenzene), formic acid, acetic acid, nitroethane, nitrobenzene, water, etc. The amount of the ether linkage cleaving agent may be normally from 1.8 to 20 equivalents to the starting compound (III). The reaction is normally effected at a temperature of −50° to 150° C., preferably of 0° to 120° C.

In the latter step, there may be used as the hydrogen halide-eliminating agent pyridine, triethylamine, N,N-dimethylaniline, N,N-diethylaniline, sodium carbonate, potassium carbonate, sodium hydrogen carbonate, sodium hydride, sodium hydroxide, potassium hydroxide, sodium methoxide, potassium ethoxide, etc. Examples of the inert solvent are benzene, toluene, xylene, dimethylformamide, dimethylsulfoxide, methanol, ethanol, acetone, methyl ethyl ketone, etc. The halide and the hydrogen halide-eliminating agent may be respectively employed in an amount of 1.8 to 4 equivalents to the compound (IV). The reaction is usually carried out at a temperature of 0° to 150° C., preferably of 20° to 100° C.

Procedure D

The diphenyl sulfone compounds of the formula:

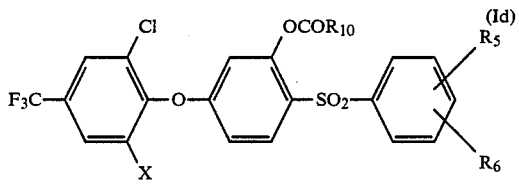

wherein $R_{10}$ is a lower alkyl group or a halo(lower)alkyl group and $R_5$, $R_6$ and X are each as defined above can be produced by reacting the compound (Ia) with an acid halide of the formula:

$$R_{10}COQ$$

wherein Q is a halogen atom and $R_{10}$ is as defined above in an inert solvent in the presence of a hydrogen halide-eliminating agent.

Examples of the inert solvent are benzene, toluene, xylene, chloroform, dichloroethane, chlorobenzene, dichlorobenzene, diethyl ether, dioxane, tetrahydrofuran, diethylene glycol dimethyl ether, acetone, methyl ethyl ketone, methyl isobutyl ketone, isophorone, cyclohexanone, ethyl acetate, methyl acetate, butyl acetate, nitroethane, nitrobenzene, acetonitrile, isobutyronitrile, pyridine, triethylamine, N,N-diethylaniline, tributylamine, N-methylmorpholine, etc. As the hydrogen halide-eliminating agent, there may be exemplified pyridine, triethylamine, N,N-dimethylaniline, N,N-diethylaniline, sodium carbonate, potassium carbonate, sodium hydrogen carbonate, etc. The acid halide is ordinarily used in an amount of 0.9 to 1.5 equivalents to the compound (Ia). The reaction is normally effected at a temperature of −20° to 100° C., preferably of 0° to 60° C.

Procedure E

The diphenyl sulfone compounds of the formula:

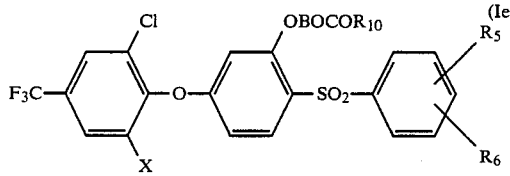

wherein B is a lower alkylene group and $R_5$, $R_6$, $R_{10}$ and X are each as defined above can be produced by reacting a compound of the formula:

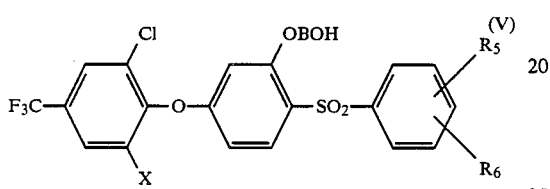

wherein B, $R_5$, $R_6$ and X are each as defined above with an acid halide of the formula:

$R_{10}COQ$ wherein $R_{10}$ and Q are each as defined above in an inert solvent in the presence of a hydrogen halide-eliminating agent.

Examples of the inert solvent are benzene, toluene, xylene, chloroform, dichloroethane, chlorobenzene, dichlorobenzene, diethyl ether, dioxane, tetrahydrofuran, diethylene glycol dimethyl ether, acetone, methyl ethyl ketone, methyl isobutyl ketone, isophorone, cyclohexanone, ethyl acetate, methyl acetate, butyl acetate, nitroethane, nitrobenzene, acetonitrile, isobutyronitrile, pyridine, triethylamine, N,N-diethylaniline, tributylamine, N-methylmorpholine, etc. As the hydrogen halide-eliminating agent, there may be exemplified pyridine, triethylamine, N,N-dimethylaniline, N,N-diethylaniline, sodium carbonate, potassium carbonate, sodium hydrogen carbonate, etc. Usually, the acid halide is employed in an amount of 0.9 to 1.5 equivalents to the compound (V). The reaction may be performed at a temperature of $-20°$ to $100°$ C., preferably of $0°$ to $60°$ C.

Procedure F

The diphenyl sulfone compounds of the formula:

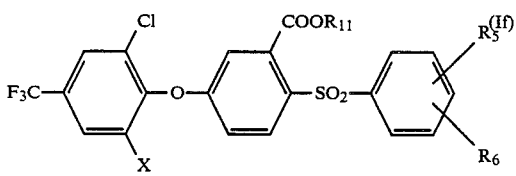

wherein $R_{11}$ is a lower alkyl group and $R_5$, $R_6$ and X are each as defined above can be produced by reacting a compound of the formula:

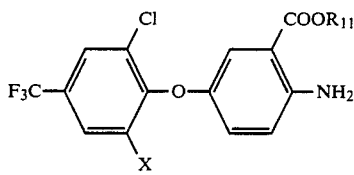

wherein $R_{11}$ and X are each as defined above with a diazotiating agent and sulfur dioxide in the presence of a copper catalyst in an inert solvent and reacting the resulting compound of the formula:

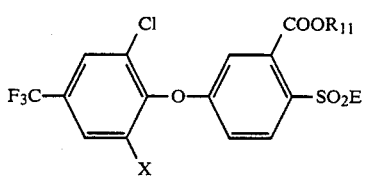

wherein E is a halogen atom and $R_{11}$ and X are each as defined above with a phenyl halide of the formula:

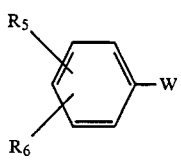

wherein W is a halogen atom and $R_5$ and $R_6$ are each as defined above in the presence of magnesium in an inert solvent.

In the former step, the combination of a nitrite (e.g. sodium nitrite) and a mineral acid (e.g. hydrochloric acid) may be employed as the diazotiating agent. It is usually employed in an amount of 0.9 to 1.2 equivalents to the compound (VI). Examples of the copper catalyst are metallic copper, copper oxide, copper chloride, etc. The reaction is ordinarily carried out at a temperature of $-5°$ to $10°$ C., preferably of $0°$ to $5°$ C., for the diazotiation and at a temperature of $-5°$ to $50°$ C., preferably of $0°$ to $30°$ C. for the sulfonylation.

In the latter step, i.e. the Grignard reaction, magnesium is normally employed in the form of powder, ribbons, flakes, etc. Its amount may be from 0.9 to 1.5 equivalents to the compound (VII). Examples of the inert solvent are diethyl ether, tetrahydrofuran, etc. The reaction proceeds usually at a temperature of $-30°$ to $80°$ C., preferably of $-20°$ to $30°$ C. When desired, any reaction aid such as dilithium tetrachlorocuprate may be present in the reaction system.

Procedure G

The diphenyl sulfone compounds of the formula:

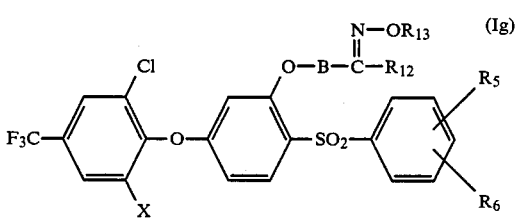

wherein $R_{12}$ is a lower alkyl group, $R_{13}$ is a hydrogen atom or a lower alkyl group and $R_5$, $R_6$, B and X are each as defined above can be produced by reacting a compound of the formula:

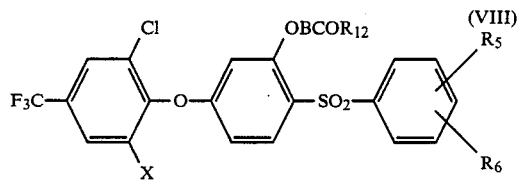

wherein $R_5$, $R_6$, $R_{12}$, B and X are each as defined above with an amine of the formula:

wherein $R_{13}$ is as defined above in an inert solvent.

In the above reaction, the amine may be employed in a free form or a salt form. When employed in a salt form such as a salt with a mineral acid (e.g. hydrochloric acid, hydrobromic acid, sulfuric acid), the simultaneous use of a base (e.g. pyridine, triethylamine, N,N-diethylaniline, sodium hydroxide, potassium hydroxide, sodium carbonate, potassium carbonate, sodium hydrogen carbonate, sodium acetate, sodium methoxide, sodium ethoxide) is favorable. The amount of the amine may be from 0.9 to 1.5 equivalents to the compound (VIII). The amount of the base to be used together with the amine in a salt form may be from 0.9 to 1.5 equivalents to the compound (VIII). Examples of the iner solvent are benzene, toluene, xylene, chloroform, dichloroethane, chlorobenzene, dichlorobenzene, diethyl ether, dioxane, tetrahydrofuran, methanol, ethanol, isopropanol, cyclohexanol, methyl celosolve, nitrobenzene, pyridine, triethylamine, N,N-diethylaniline, tributylamine, N-methylmorpholine, etc. The reaction temperature is normally from 0° to 120° C., preferably from 30° to 80° C.

Practical and presently preferred embodiments for the production of the diphenyl sulfone compounds (I) as well as that of the starting materials are shown in the following Examples and Reference Examples.

EXAMPLE 1

To a solution of 4-(2-chloro-4-trifluoromethylphenoxy)-2-ethoxy-4'-chlorodiphenyl sulfone (6 g) in dichloromethane (60 ml), a solution of boron tribromide (3.4 g) in dichloromethane (15 ml) was dropwise added while sitrring at room temperature. After allowed to react overnight, the reaction mixture was washed with 5% aqueous hydrochloric acid and water in order. The organic layer was concentrated to give an oily substance, which was purified by column chromatography on silica gel and recrystallized from a mixture of toluene and hexane to give 4.3 g of 4-(2-chloro-4-trifluoromethylphenoxy)-2-hydroxy-4'-chlorodiphenyl sulfone. M.P., 76.5°–77.5° C.

EXAMPLE 2

To a solution of 4-(2-chloro-4-trifluoromethylphenoxy)-2-ethoxy-4'-methyldiphenyl sulfone (9 g) in dichloromethane (90 ml), a solution of boron tribromide (5 g) in dichlorometane (15 ml) was dropwise added while stirring at room temperature. After allowed to react overnight, the reaction mixture was washed with 5% aqueous hydrochloric acid and water in order. The organic layer was concentrated to give an oily substance, which was purified by column chromatography on silica gel and recrystallized from a mixture of toluene and hexane to give 5.9 g of 4-(2-chloro-4-trifluoromethylphenoxy)-2-hydroxy-4'-methyldiphenyl sulfone. M.P., 87.5°–91° C.

EXAMPLE 3

To a solution of 4-(2-chloro-4-trifluoromethylphenoxy)-2-methoxy-4'-methyldiphenyl sulfone (2 g) in dichloromethane (20 ml), a solution of boron tribromide (1.1 g) in dichlorometane (10 ml) was dropwise added while stirring at room temperature. After allowed to react overnight, the reaction mixture was washed with 5% aqueous hydrochloric acid and water in order. The organic layer was concentrated to give an oily substance, which was purified by column chromatography on silica gel and recrystallized from a mixture of toluene and hexane to give 1.3 g of 4-(2-chloro-4-trifluoromethylphenoxy)-2-hydroxy-4'-methyldiphenyl sulfone. M.P., 87.5°–91° C.

EXAMPLE 4

To a solution of 4-(2-chloro-4-trifluoromethylphenoxy)-2-ethoxy-4'-methoxydiphenyl sulfone (7.85 g) in dichloromethane (80 ml), a solution of boron tribromide (4.85 g) in dichloromethane (15 ml) was dropwise added while sitrring at room temperature. After allowed to react overnight, the reaction mixture was washed with 5% aqueous hydrochloric acid and water in order. The organic layer was concentrated to give an oily substance, which was purified by column chromatography on silica gel to give 2.8 g of a solid substance (from the dichloromethane eluate). This was recrystallized from a mixture of toluene and hexane to give 2.08 g of 4-(2-chloro-4-trifluoromethylphenoxy)-2-hydroxy-4'-methoxydiphenyl sulfone. M.P., 100°–101.5° C. Further elution with a mixture of acetone and hexane (2:5) gave 3.9 g of 4-(2-chloro-4-trifluoromethylphenoxy)-2,4'-dihydroxydiphenyl sulfone as a resinous product.

EXAMPLE 5

4-(2-Chloro-4-trifluoromethylphenoxy)-2-hydroxy-4'-methyldiphenyl sulfone (1 g), chloroacetonitrile (0.2 g) and potassium carbonate (0.17 g) were added to dimethylformamide (15 ml), and the resulting mixture was allowed to react at 60° C. for 3 hours. A saturated sodium chloride solution was added thereto, and the reaction mixture was extracted with toluene. The toluene layer was concentrated, and the residue was purified by silica gel column chromatography, followed by recrystallization from ethanol to give 0.85 g of 4-(2-chloro-4-trifluoromethylphenoxy)-2-cyanomethoxy-4'-methyldiphenyl sulfone. M.P., 98.5°–99.5° C.

EXAMPLE 6

4-(2-Chloro-4-trifluoromethylphenoxy)-2-hydroxy-4'-methyldiphenyl sulfone (0.8 g), bromomethoxyacetonitrile (0.285 g) and potassium carbonate (0.13 g) were added to dimethylformamide (15 ml), and the resultant mixture was allowed to react at 60° C. for 3 hours. A saturated sodium chloride solution was added thereto, and the reaction mixture was extracted with toluene. The toluene layer was concentrated, and the residue was purified by silica gel column chromatography to give 0.78 g of a solid substance. Recrystallization from ethanol gave 0.58 g of 4-(2-chloro-4-trifluoromethylphenoxy)-2-(1-methoxy-1-cyanomethoxy)-4'-methyldiphenyl sulfone. M.P., 139°–141.5° C.

EXAMPLE 7

4-(2-Chloro-4-trifluoromethylphenoxy)-2-hydroxy-4'-methoxydiphenyl sulfone (1 g), ethyl bromoacetate (0.44 g) and potassium carbonate (0.25 g) were added to dimethylformamide (15 ml), and the resultant mixture was allowed to react at 60° C. for 3 hours. A saturated sodium chloride solution was added thereto, and the reaction mixture was extracted with toluene. The toluene layer was concentrated, and the residue was purified by silica gel column chromatography. The thus obtained solid substance was recrystallized from ethanol to give 0.7 g of 4-(2-chloro-4-trifluoromethylphenoxy)-2-ethoxycarbonylmethoxy-4'-methoxydiphenyl sulfone. M.P., 111.5°–113° C.

EXAMPLE 8

4-(2-Chloro-4-trifluoromethylphenoxy)-2-hydroxy-4'-methoxydiphenyl sulfone (1 g), methyl-bromopropionate (0.6 g) and potassium carbonate (0.25 g) were added to dimethylformamide (15 ml), and the resultant mixture was allowed to react at 60° C. for 3 hours. Work-up as in Example 7 gave 0.9 g of 4-(2-chloro-4-trifluoromethylphenoxy)-2-(1-methoxycarbonylethoxy)-4'-methoxydiphenyl sulfone as a resinous material.

EXAMPLE 9

4-(2-Chloro-4-trifluoromethylphenoxy)-2-hydroxy-4'-methoxydiphenyl sulfone (4 g), ethylene bromohydrin (1.2 g) and potassium carbonate (0.66 g) were added to dimethylformamide (15 ml), and the resultant mixture was allowed to react at 60° C. for 3 hours. A saturated sodium chloride solution was added thereto, and the reaction mixture was extracted with toluene. The toluene layer was concentrated, and the residue was purified by silica gel column chromatography to give 1.6 g of 4-(2-cloro-4-trifluoromethylphenoxy)-2-(2-hydroxyethoxy)-4'-methoxydiphenyl sulfone as a resinous material.

EXAMPLE 10

4-(2-Chloro-4-trifluoromethylphenoxy)-2-hydroxy-4'-methyldiphenylsulfone (1.5 g), acetyl chloride (1 g) and triethylamine (0.41 g) were added to tetrahydrofuran (20 ml), and the resultant mixture was allowed to react at room temperature. After allowed to stand overnight, the reaction mixture was concentrated, water was added thereto, and the resulting mixture was extracted with toluene. The extract was concentrated, and the residue was purified by silica gel column chromatography. Recrystallization from ethanol gave 0.7 g of 4-(2-chloro-4-trifluoromethylphenoxy)-2-acetyloxy-4'-methyldiphenyl sulfone. M.P., 115°–119° C.

EXAMPLE 11

4-(2-Chloro-4-trifluoromethylphenoxy)-2-(2-hydroxyethoxy)-4'-methoxydiphenyl sulfone (1 g), acetyl chloride (0.5 g) and triethylamine (0.2 g) were added to tetrahydrofuran (20 ml), and the resultant mixture was allowed to react at room temperature. After allowed to stand overnight, the reaction mixture was concentrated, water was added thereto, and the resulting mixture was extracted with toluene. The extract was concentrated, and the residue was purified by silica gel column chromatography, followed by recrystallization from ethanol to give 0.74 g of 4-(2-chloro-4-trifluoromethylphenoxy)-2-(2-acetyloxyethoxy)-4'-methoxydiphenyl sulfone as a resinous material.

EXAMPLE 12

4-(2-Chloro-4-trifluoromethylphenoxy)-2,4'-dihydroxy-diphenyl sulfone (1.5 g), propargyl bromide (0.88 g) and potassium carbonate (0.51 g) were added to dimethylformamide (15 ml), and the resultant mixture was allowed to react at 60° C. for 3 hours. A saturated sodium chloride solution was added thereto, and the reaction mixture was extracted with toluene. The extract was concentrated, and the residue was purified by silica gel column chromatography to give 1.43 g of 4-(2-chloro-4-trifluoromethylphenoxy)-2,4'-dipropargyloxyphenyl sulfone as a resinous material.

EXAMPLE 13

(a) Ethyl 5-(2-chloro-4-trifluoromethylphenoxy)-2-aminobenzoate hydrochloride (12 g) and conc. hydrochloric acid (6.6 ml) were added to acetic acid (85 ml), and the resultant mixture was cooled to less than 10° C. A solution of sodium nitrite (2.5 g) in water (6 ml) was dropwise added thereto. When the resulting mixture became completely transparent, benzene (20 ml), acetic acid (20 ml) saturated with sulfur dioxide and copper chloride (1.5 g) were added thereto. After stirring overnight, the reaction mixture was poured onto ice-water. The deposited oily substance was extracted with chloroform, washed with water and dried over anhydrous magnesium sulfate. The extract was concentrated and allowed to stand. The crystallized substance was recrystallized from hexane to give 9 g of 4-(2-chloro-4-trifluoromethylphenoxy)-2-ethoxycarbonylbenzenesulfonyl chloride. M.P., 96°–96.5° C.

(b) p-Methoxybenzenemagnesium bromide produced by reacting p-bromoanisole (1.14 g) with magnesium (0.15 g) in anhydrous tetrahydrofuran (20 ml) was dropwise added to anhydrous tetrahydrofuran (20 ml) containing 4-(2-chloro-4-trifluoromethylphenoxy)-2-ethoxycarbonylbenzenesulfonyl chloride (2.5 g) obtained in (a) and dilithium tetrachlorocuprate (0.1 mmol) at −20° C. After 1 hour, the reaction temperature was brought to room temperature, and stirring was continued for 1.5 hours to complete the reaction.

A 5% aqueous hydrochloric acid was added to the reaction mixture, which was then extracted with ethyl acetate. The extract was concentrated, and the residue was purified by thin layer chromatography using silica gel and a mixture of acetone and hexane (1:5) to give 0.6 g of 4-(2-chloro-4-trifluoromethylphenoxy)-2-ethoxycarbonyl-4'-methoxydiphenyl sulfone as an oily substance. $n_D^{20}$ 1.5426.

EXAMPLE 14

4-(2-Chloro-4-trifluoromethylphenoxy)-2-(2-oxo-n-propoxy)-4'-fluorodiphenyl sulfone (0.48 g), o-methylhydroxylamine (0.1 g) and sodium hydroxide (0.05 g) were added to ethanol (10 ml), and the resultant mixture was allowed to react at 60° C. for 3 hours. A saturated sodium chloride solution was added to the reaction mixture, followed by extraction with toluene. The extract was concentrated, and the residue was purified by silica gel chromatography to give 0.43 g of 4-(2-chloro-4trifluoromethylphenoxy)-2-(2-methoxyimino-n-propoxy)-4'-fluorodiphenyl sulfone as a resinous material.

REFERENCE EXAMPLE 1

4-(2-Chloro-4-trifluoromethylphenoxy)-2-methoxyaniline (10 g) was added to a mixture of water (50 ml) and conc. hydrochloric acid (8 ml). To the resultant mixture maintained at 0°–5° C., a solution of sodium nitrite (2.4 g) in water (10 ml) was dropwise added. After completion of the addition, the reaction mixture was stirred for 1 hour and neutralized with sodium acetate. The resulting mixture was dropwise added to a mixture of p-methylbenzenethiol (3.9 g), sodium hydroxide (3.5 g), water (20 ml) and copper powder (0.8 g) kept at 40° C., and the resultant mixture was heated to about 100° C. for 1 hour. The reaction mixture was extracted with ether, and the extract was washed with 10% sodium hydroxide solution, water, 5% hydrochloric acid and water in order and concentrated. The resulting oily substance was purified by silica gel column chromatography to give 10 g of 4-(2-chloro-4-trifluoromethylphenoxy)-2-methoxy-4'-methyldiphenyl sulfide.

4-(2-Chloro-4-trifluoromethylphenoxy)-2-methoxy-4'-methyldiphenyl sulfide (10 g) as obtained above was dissolved in acetic acid (120 ml), and 30% aqueous hydrogen peroxide (14 g) was dropwise added thereto while stirring. After completion of the addition, stirring was continued at 40° C. for 3 hours. To the reaction mixture, 5% aqueous sodium thiosulfite solution was added thereto, and the resultant mixture was concentrated and extracted with toluene. The extract was washed with 5% sodium hydroxide solution and water in order, dried over anhydrous magnesium sulfate and concentrated to give an oily substance, which was purified by silica gel column chromatography and crystallized from ethanol. Recrystallization from ethanol gave 2.8 g of 4-(2-chloro-4-trifluoromethylphenoxy)-2-methoxy-4'-methyldiphenyl sulfone. M.P., 156.5°–159.5° C.

REFERENCE EXAMPLE 2

4-(2-Chloro-4-trifluoromethylphenoxy)-2-methoxyaniline (9.6 g) was added to a mixture of water (50 ml) and conc. hydrochloric acid (8 ml). To the resultant mixture maintained at 0°–5° C., a solution of sodium nitrite (2.4 g) in water (10 ml) was dropwise added. After completion of the addition, the reaction mixture was stirred for 1 hour and neutralized with sodium acetate. The resulting mixture was dropwise added to a mixture of p-chlorobenzenethiol (4.6 g), sodium hydroxide (3.5 g), water (30 ml) and copper powder (0.6 g) kept at 40° C., heated to about 100° C. and allowed to react for 1 hour. The reaction mixture was extracted with ether, washed with 10% sodium hydroxide solution, water, 5% hydrochloric acid and water in order and concentrated to give an oily substance. Purification by silica gel column chromatography gave 10 g of 4-(2-chloro-4-trifluoromethylphenoxy)-2-methoxy-4'-chlorodiphenyl sulfide.

4-(2-Chloro-4-trifluoromethylphenoxy)-2-methoxy-4'-chlorodiphenyl sulfide (7 g) as obtained above was dissolved in acetic acid (120 ml), 30% aqueous hydrogen peroxide (10 g) was dropwise added thereto, and the resultant mixture was allowed to react at 40° C. for 3 hours. After completion of the reaction, 5% aqueous sodium thiosulfite solution was added thereto. The reaction mixture was concentrated and extracted with toluene. The extract was washed with 5% sodium hydroxide solution and water in order, dried over anhydrous magnesium sulfate and concentrated to give an oily substance. The oily substance was purified by column chromatography on silica gel and crystallized from ethanol. Recrystallization from ethanol gave 2.9 g of 4-(2-chloro-4-trifluoromethylphenoxy)-2-methoxy-4'-chlorodiphenyl sulfone. M.P., 125°–130° C.

REFERENCE EXAMPLE 3

4-(2-Chloro-4-trifluoromethylphenoxy)-2-ethoxy-4'-methoxydiphenyl sulfide (40 g) prepared as in Reference Example 2 was dissolved in acetic acid (200 ml), and the resultant solution was dropwise added to 30% aqueous hydrogen peroxide (56 g) while stirring, and the resulting mixture was allowed to react at 50° C. for 3 hours. After completion of the reaction, 5% aqueous sodium thiosulfite solution was added thereto. The reaction mixture was concentrated and extracted with toluene. The extract was washed with 5% sodium hydroxide solution and water in order, dried over anhydrous magnesium sulfate and concentrated to give an oily substance. The oily substance was purified by silica gel column chromatography and crystallized from ethanol. Recrystallization from ethanol gave 11.4 g of 4-(2-chloro-4-trifluoromethylphenoxy)-2-ethoxy-4'-methoxydiphenyl sulfone. M.P., 101°–102° C.

REFERENCE EXAMPLE 4

2-Chloro-3'-ethoxy-4-trifluoromethyldiphenyl ether 3 g; purity, ca. 92%) and 4-methoxybenzenesulfonyl chloride (2.15 g) were dissolved in 1,2-dichloroethane (15 ml), followed by addition of anhydrous ferric chloride (1.96 g). The resultant mixture was refluxed for 1 hour. To the reaction mixture, 5% aqueous hydrochloric acid was added, and the resultant mixture was extracted with toluene. The extract was washed with water and concentrated to give an oily substance. Purification by silica gel column chromatography and recrystallization from ethanol gave 1.4 g of 4-(2-chloro-4-trifluoromethylphenoxy)-2-ethoxy-4'-methoxydiphenyl sulfone. M.P., 101°–102° C.

Some examples of the diphenyl sulfone compound (I) produced in the same manner as above are shown in Table 1.

TABLE 1

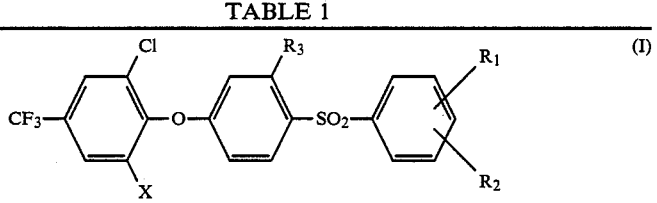

| Compound No. | $R_1$, $R_2$ | $R_3$ | X | Physical property |
|---|---|---|---|---|
| 1 | H | OH | H | M.P. 104.5–105.5° C. |

TABLE 1-continued (I) Structure: 2-Cl, 4-CF$_3$, 6-X phenyl — O — (phenyl with R$_3$) — SO$_2$ — (phenyl with R$_1$, R$_2$)

| Compound No. | R$_1$, R$_2$ | R$_3$ | X | Physical property |
|---|---|---|---|---|
| 2 | 4-CH$_3$ | OH | H | M.P. 87.5–91° C. |
| 3 | 4-Cl | OH | H | M.P. 76.5–77.5° C. |
| 4 | 4-Br | OH | H | M.P. 86.5–88° C. |
| 5 | 4-F | OH | H | M.P. 71.5–72.5° C. |
| 6 | 4-CH$_3$O | OH | H | M.P. 100–101.5° C. |
| 7 | 4-CH$_3$O | OCH$_2$CH=CH$_2$ | H | Resinous |
| 8 | 4-CH$_3$O | OCH$_2$C≡CH | H | Resinous |
| 9 | 4-CH≡CCH$_2$O | OCH$_2$C≡CH | H | Resinous |
| 10 | 4-CH$_3$ | OCH$_2$CN | H | M.P. 98.5–99.5° C. |
| 11 | 4-CH$_3$ | OCH(OCH$_3$)CN | H | M.P. 139–141.5° C. |
| 12 | 4-Br | OCH(OCH$_3$)CN | H | M.P. 108–111° C. |
| 13 | H | OCH$_2$CH$_2$Cl | H | M.P. 100.5–106.5° C. |
| 14 | H | OCH$_2$COCH$_3$ | H | M.P. 112–113.5° C. |
| 15 | 4-CH$_3$O | OCH$_2$COOH | H | Resinous |
| 16 | 4-CH$_3$O | OCH$_2$COOCH$_3$ | H | M.P. 94–95° C. |
| 17 | 4-CH$_3$ | OCH$_2$COOCH$_3$ | H | M.P. 121.5–125° C. |
| 18 | H | OCH$_2$COOCH$_3$ | H | M.P. 140.5–142° C. |
| 19 | 4-CH$_3$O | OCH$_2$COOC$_2$H$_5$ | H | M.P. 111.5–113° C. |
| 20 | 4-CH$_3$ | OCH$_2$COOC$_2$H$_5$ | H | M.P. 136.5–138.5° C. |
| 21 | 4-Cl | OCH$_2$COOC$_2$H$_5$ | H | M.P. 109–110° C. |
| 22 | H | OCH$_2$COOC$_3$H$_7$(iso) | H | M.P. 114–115° C. |
| 23 | 4-Cl | OCH$_2$COOCH$_2$CH$_2$Cl | H | M.P. 109–110° C. |
| 24 | H | OCH$_2$COOCH$_2$CH=CH$_2$ | H | M.P. 116.5–119° C. |
| 25 | 4-CH$_3$ | OCH$_2$COOCH$_2$COOC$_2$H$_5$ | H | Resinous |
| 26 | 4-CH$_3$ | OCH$_2$COON=C(CH$_3$)$_2$ | H | M.P. 188–189° C. |
| 27 | 4-Cl | OCH$_2$CON(CH$_3$)$_2$ | H | M.P. 163.5–165° C. |
| 28 | 4-CH$_3$O | OCH(CH$_3$)COOCH$_3$ | H | Resinous |
| 29 | 4-Cl | OCH(CH$_3$)COOC$_2$H$_5$ | H | Resinous |
| 30 | 4-CH$_3$OOCCHO(CH$_3$) | OCH(CH$_3$)COOCH$_3$ | H | Resinous |
| 31 | 4-CH$_3$O | OCH$_2$CH$_2$OH | H | Resinous |
| 32 | 4-CH$_3$O | OCH$_2$CH$_2$OCOCH$_3$ | H | Resinous |
| 33 | 4-CH$_3$ | OCOCH$_3$ | H | M.P. 115–119° C. |
| 34 | 4-CH$_3$ | COOC$_2$H$_5$ | H | n$_D^{18}$ 1.5455 |
| 35 | 4-CH$_3$O | COOC$_2$H$_5$ | H | n$_D^{20}$ 1.5426 |
| 36 | 4-Br | OCH$_2$CH$_2$OC$_2$H$_5$ | H | Resinous |
| 37 | 4-Br | OCH(OCH$_3$)COOCH$_3$ | H | Resinous |
| 38 | 4-CH$_2$=CHCH$_2$O | OCH$_2$CH=CH$_2$ | H | Resinous |
| 39 | H | OCH$_2$CN | H | M.P. 110.5–111.5° C. |
| 40 | 4-F | OCH$_2$CN | H | M.P. 111–112° C. |
| 41 | 4-Br | OCH$_2$CN | H | M.P. 127.5–128.5° C. |
| 42 | 4-CH$_3$O | OCH$_2$CN | H | M.P. 142–143° C. |

TABLE 1-continued $$\text{(I)}$$

Structure: 2-Cl, 4-CF$_3$, 6-X substituted phenyl — O — (phenyl with R$_3$) — SO$_2$ — (phenyl with R$_1$, R$_2$)

| Compound No. | R$_1$, R$_2$ | R$_3$ | X | Physical property |
|---|---|---|---|---|
| 43 | 4-C$_2$H$_5$ | OCH$_2$CN | H | Resinous |
| 44 | H | OCHCN / OCH$_3$ | H | M.P. 105.5–106.5° C. |
| 45 | 4-F | OCHCN / OCH$_3$ | H | M.P. 97–98° C. |
| 46 | 4-Cl | OCHCN / OCH$_3$ | H | M.P. 108.5–109.5° C. |
| 47 | 4-CH$_3$O | OCHCN / OCH$_3$ | H | M.P. 103–104° C. |
| 48 | 4-C$_2$H$_5$ | OCHCN / OCH$_3$ | H | M.P. 95–96° C. |
| 49 | 4-F | OCH$_2$COCH$_3$ | H | M.P. 113–114.5° C. |
| 50 | 4-CH$_3$O | OCH$_2$COCH$_3$ | H | M.P. 135–136° C. |
| 51 | 4-C$_2$H$_5$ | OCH$_2$COCH$_3$ | H | M.P. 120.5–121.5° C. |
| 52 | 4-F | OCH$_2$COOCH$_3$ | H | M.P. 117–118° C. |
| 53 | 4-C$_2$H$_5$ | OCH$_2$COOCH$_3$ | H | Resinous |
| 54 | 4-F | OCHCOOCH$_3$ / CH$_3$ | H | M.P. 96.5–97.5° C. |
| 55 | H | OCHCOOCH$_3$ / OCH$_3$ | H | M.P. 121–122° C. |
| 56 | 4-F | OCHCOOCH$_3$ / CH$_3$ | H | Resinous |
| 57 | 4-CH$_3$ | OCHCOOCH$_3$ / CH$_3$ | H | M.P. 90.5–91.5° C. |
| 58 | 4-C$_2$H$_5$ | OCHCOOCH$_3$ / CH$_3$ | H | $n_D^{28.5}$ 1.5465 |
| 59 | 4-CH$_3$O | OCHCOOCH$_3$ / OCH$_3$ | H | M.P. 98–99° C. |
| 60 | 4-CH$_3$O | OCHCOOC$_3$H$_7$(iso) / OCH$_3$ | H | Resinous |
| 61 | 4-Cl | OCH$_2$CN | H | M.P. 110.5–112° C. |
| 62 | 4-Cl | OCH$_2$COOCH$_3$ | H | M.P. 124.5–125.5° C. |
| 63 | 4-CH$_3$ | OCH$_2$COOCH$_2$CN | H | M.P. 51–52° C. |
| 64 | 4-CH$_3$O | OCHCOOCH$_2$CN / CH$_3$ | H | Resinous |
| 65 | 4-CH$_3$O | OCH$_2$COOCH$_2$CH$_2$OCH$_3$ | H | Resinous |
| 66 | 4-F | OCH$_2$CH$_2$OC$_2$H$_5$ | H | M.P. 99–100° C. |
| 67 | 4-CH$_3$O | OCH$_2$CH$_2$OC$_2$H$_5$ | H | M.P. 104.5–105.5° C. |
| 68 | 4-CH$_3$ | OCH$_2$CH$_2$OCH=CH$_2$ | H | M.P. 58–59° C. |
| 69 | 4-CH$_3$ | OCH$_2$OCH$_2$ | H | M.P. 84–87° C. |
| 70 | 4-CH$_3$ | OCH$_2$SCH$_3$ | H | Resinous |
| 71 | 4-CH$_3$ | OCH$_2$CH$_2$SCH$_3$ | H | $n_D^{27}$ 1.5743 |
| 72 | 4-CH$_3$ | OCH$_2$CH$_2$SC$_2$H$_5$ | H | $n_D^{27}$ 1.5670 |

TABLE 1-continued $$\text{(I)}$$

Structure (I): 2-Cl, 4-CF₃, 6-X substituted phenyl ether linked via O to a phenyl bearing R₃ and SO₂-(phenyl with R₁, R₂)

| Compound No. | R₁, R₂ | R₃ | X | Physical property |
|---|---|---|---|---|
| 73 | 4-CH₃ | OCH(CH₃)COCH₃ | H | Resinous |
| 74 | 4-F | OCH₂COCH₃ | H | M.P. 113–114.5° C. |
| 75 | 4-CH₃O | OCH₂COCH₃ | H | M.P. 135–136° C. |
| 76 | 4-F | OCH₂C(CH₃)=NOH | H | M.P. 141.5–142.5° C. |
| 77 | 4-CH₃O | OCH₂C(CH₃)=NOCH₃ | H | Resinous |
| 78 | 4-CH₃ | (γ-butyrolactone-2-yloxy) | H | M.P. 69–69.5° C. |
| 79 | 4-C₂H₅ | OH | H | M.P. 67–68° C. |
| 80 | 4-CH₃O | OCH₂CH₂N(CH₃)₂ | H | M.P. 118.5–119.5° C. |
| 81 | 4-CH₃O | OCH₂CH₂N(C₂H₅)₂ | H | M.P. 70–71° C. |
| 82 | 4-CH₃O | OCH(OCH₃)COOC₅H₁₁ | H | $n_D^{27.2}$ 1.5333 |
| 83 | 4-F | OCH₂CH=CHCOOCH₃ | H | Resinous |
| 84 | 4-F | OSO₂CH₃ | H | M.P. 137–138° C. |
| 85 | 4-F | OP(=O)(OC₂H₅)₂ | H | $n_D^{27.3}$ 1.5382 |
| 86 | 4-CH₃ | OCOOCH₃ | H | M.P. 113–118° C. |
| 87 | 4-CH₃ | OCH₂COSC₂H₅ | H | M.P. 108.5–110° C. |
| 88 | 4-CH₃O | OCH₂COOCH₂C≡CH | H | Resinous |
| 89 | 4-CH₃ | OCH(CH₃)COOCH₃ | H | Resinous |
| 90 | 4-CH₃ | OCH(CH₃)COOC₂H₅ | H | M.P. 97–98° C. |
| 91 | 4-Br | OCH₂COOCH₃ | H | M.P. 115–116° C. |
| 92 | 4-Br | OCH₂COOC₂H₅ | H | M.P. 100–102° C. |
| 93 | 4-CH₃ | OH | Cl | M.P. 162–163° C. |
| 94 | 4-CH₃ | OCH₂COOCH₃ | Cl | M.P. 164.5–166° C. |
| 95 | 4-CH₃ | OCH(CH₃)COOC₂H₅ | Cl | M.P. 120–125° C. |
| 96 | 4-CH₃ | OCH₂CN | Cl | M.P. 142–143° C. |

TABLE 1-continued $$\text{(I)}$$

Structure: 2-Cl, 4-CF$_3$, 6-X phenyl — O — phenyl(R$_3$) — SO$_2$ — phenyl(R$_1$, R$_2$)

| Compound No. | R$_1$, R$_2$ | R$_3$ | X | Physical property |
|---|---|---|---|---|
| 97 | 4-CH$_3$ | OCHCN<br>\|<br>OCH$_3$ | Cl | M.P. 153–154.5° C. |
| 98 | 4-CH$_3$ | OCHCOOCH$_3$<br>\|<br>OCH$_3$ | Cl | M.P. 103.5–105° C. |
| 99 | 4-C$_2$H$_5$O | OH | H | M.P. 93–95° C. |
| 100 | 4-F | OCH$_2$COOC$_2$H$_5$ | H | M.P. 103–104.5° C. |
| 101 | 4-C$_2$H$_5$O | OCH$_2$COOCH$_3$ | H | M.P. 114.5–116° C. |
| 102 | 4-C$_2$H$_5$O | OCHCOOC$_2$H$_5$<br>\|<br>CH$_3$ | H | Resinous |
| 103 | 4-C$_2$H$_5$O | OCHCOOCH$_3$<br>\|<br>OCH$_3$ | H | Resinous |
| 104 | 4-C$_2$H$_5$O | OCHCOCH$_3$<br>\|<br>CH$_3$ | H | Resinous |
| 105 | 4-CH$_3$ | (tetrahydropyran-2-yloxy) | H | M.P. 83.5–88° C. |
| 106 | 4-CH$_3$ | OCH$_2$COCH$_2$CH$_3$ | Cl | M.P. 132–134° C. |
| 107 | 4-CH$_3$ | OCH$_2$COOC$_2$H$_5$ | Cl | M.P. 104–106° C. |
| 108 | 4-CH$_3$ | OCH$_2$OCH$_3$ | Cl | M.P. 132–135° C. |
| 109 | 4-CH$_3$ | OCH$_2$SCH$_3$ | Cl | M.P. 154–156° C. |
| 110 | 4-Cl | OCHCOOCH$_3$<br>\|<br>OCH$_3$ | H | M.P. 86–87.5° C. |
| 111 | H | OCHCOOCH$_3$<br>\|<br>CH$_3$ | H | Resinous |
| 112 | 4-Cl | OCHCOOCH$_3$<br>\|<br>CH$_3$ | H | M.P. 105–106° C. |
| 113 | 4-Br | OCHCOOCH$_3$<br>\|<br>CH$_3$ | H | M.P. 100.5–101.5° C. |
| 114 | 4-F | OCHCOCH$_3$<br>\|<br>CH$_3$ | H | Resinous |
| 115 | 4-Cl | OCHCOCH$_3$<br>\|<br>CH$_3$ | H | Resinous |
| 116 | 4-Br | OCHCOCH$_3$<br>\|<br>CH$_3$ | H | Resinous |
| 117 | H | OCHCOCH$_3$<br>\|<br>CH$_3$ | H | Resinous |
| 118 | 4-CH$_3$ | OCH$_2$CH$_2$OH | H | M.P. 114–115° C. |

TABLE 1-continued structure (I): 2-Cl, 4-CF$_3$, 6-X phenyl — O — (3-R$_3$, phenyl) — SO$_2$ — (R$_1$, R$_2$ phenyl)

| Compound No. | R$_1$, R$_2$ | R$_3$ | X | Physical property |
|---|---|---|---|---|
| 119 | 4-CH$_3$ | OCH(CH$_3$)COCH$_3$ | Cl | Resinous |
| 120 | 4-C$_3$H$_7$(n) | OH | H | M.P. 69–71.5° C. |
| 121 | 4-CH$_3$ | OCH$_2$CH$_2$OCCH$_3$ (C=O) | H | Resinous |
| 122 | 4-CH$_3$O | OCH(CH$_3$)COCH$_3$ | H | Resinous |
| 123 | 4-C$_2$H$_5$ | OCH(CH$_3$)COCH$_3$ | H | Resinous |
| 124 | 4-CH$_3$S | OH | H | M.P. 124–125° C. |
| 125 | 4-C$_3$H$_7$(n) | OCH$_2$COOCH$_3$ | H | M.P. 105.5–106.5° C. |
| 126 | 4-C$_3$H$_7$(n) | OCH(CH$_3$)COOCH$_3$ | H | $n_D^{17.2}$ 1.5400 |
| 127 | 4-CH$_3$S | OCH$_2$COOCH$_3$ | H | Resinous |
| 128 | 2,5-(CH$_3$)$_2$ | OH | H | M.P. 174–175° C. |
| 129 | 2,4-(CH$_3$)$_2$ | OH | H | M.P. 64.5–66.5° C. |
| 130 | 3,4-(CH$_3$)$_2$ | OH | H | M.P. 88–89° C. |
| 131 | 2,4-(CH$_3$)$_2$ | OCH$_2$COOCH$_3$ | H | M.P. 111–113° C. |
| 132 | 3,4-(CH$_3$)$_2$ | OCH$_2$COOCH$_3$ | H | M.P. 104–105° C. |
| 133 | 4-(C$_6$H$_4$)-O- | OH | H | M.P. 110–113° C. |
| 134 | 4-CH$_3$ | OCHF$_2$ | H | M.P. 92.5–94° C. |
| 135 | 4-Cl | OCH$_2$CH$_2$OH | H | Resinous |
| 136 | 4-CH$_3$ | OCH$_2$COCH$_3$ | H | M.P. 71–73° C. |
| 137 | 4-CH$_3$SO$_2$ | OH | H | M.P. 77–80° C. |
| 138 | 4-CH$_3$ | OCH$_2$—C(CH$_3$)(OCH$_2$CH$_2$O) (1,3-dioxolane) | H | M.P. 135–136° C. |
| 139 | 4-Cl | OCH$_2$CH$_2$OCC$_2$H$_5$ (C=O) | H | Resinous |
| 140 | 4-CH$_3$ | OCH$_2$CC(CH$_3$)$_3$ (C=O) | H | M.P. 144.5–145.5° C. |
| 141 | 4-CH$_3$SO$_2$ | OCH$_2$COOCH$_3$ | H | M.P. 106–107° C. |
| 142 | 4-CH$_3$ | OCH$_2$CH$_2$OCC$_2$H$_5$ (C=O) | H | M.P. 109–110° C. |
| 143 | 4-CH$_3$ | OCH(CH$_3$)—C(CH$_3$)(OCH$_2$CH$_2$O) (1,3-dioxolane) | H | $n_D^{20}$ 1.5385 |
| 144 | 4-CH$_3$ | OCH$_2$CH$_2$OCCH$_2$Cl (C=O) | H | M.P. 157.5–158.5° C. |

For the practical usage of the diphenyl sulfone compounds (I) as herbicides, they may be formulated into any conventional composition form such as emulsifiable concentrates, wettable powders, suspensions, granules and dusts. The concentration of the active ingredient in such composition form is usually within a range of 0.1 to 90% by weight, preferably of 1 to 80% by weight.

In order to achieve the formulation, a solid or liquid carrier or diluent may be used. As the solid carrier or diluent, there may be employed mineral powders (e.g. kaolin, bentonite, talc, diatomaceous earth, sericite, synthetic hydrated silicon dioxide). As the liquid carrier or diluent, there may be employed aromatic hydrocarbons (e.g. xylene, methylnaphthalene), ketones (e.g., cyclohexanone, isophorone), chlorobenzene, dimethylformamide, cellosolve, ethylene glycol, water, etc.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene styrylaryl ethers, polyoxyethylene fatty acid esters, polyoxyethylene sorbitan fatty acid esters, oxyethyleneoxypropylene polymers, alkyl sulfates, alkyl sulfonates, dialkyl sulfosuccinate, alkylaryl sulfonates and the like. If necessary, lignin sulfonates, polyviyl alcohol, methylcellulose or the like may be used as an auxiliary agent.

Practical embodiments of the herbicidal composition according to the invention are illustratively shown in the following examples wherein part(s) and % are by weight. The compound number of the active ingredient corresponds to the one in Table 1.

FORMULATION EXAMPLE 1

Eighty parts of Compound No. 28, 5 parts of polyoxyethylene alkylaryl ether and 15 parts of synthetic hydrated silicon dioxide are well mixed while being powdered to obtain a wettable powder.

FORMULATION EXAMPLE 2

Ten parts of Compound No. 11, 10 parts of polyoxyethylene alkylaryl ether, 5 parts of alkylaryl sulfonate and 75 parts of cyclohexanone are well mixed while being powdered to obtain an emulsifiable concentrate.

FORMULATION EXAMPLE 3

One part of Compound No. 16, 1 part of synthetic hydrated silicon dioxide, 5 parts of ligninsulfonate and 93 parts of clay are well mixed while being powdered. The mixture is then kneaded with water, granulated and dried to obtain granules.

FORMULATION EXAMPLE 4

Three parts of Compound No. 21, 0.5 part of isopropyl acid phosphate, 66.5 parts of clay and 30 parts of talc are well mixed while being powdered to obtain a dust.

FORMULATION EXAMPLE 5

Twenty parts of Compound No. 10 is mixed with 60 parts of an aqueous solution containing 3% polyoxyethylene sorbitan monooleate and pulverized until the particle size of the active ingredient becomes less than 3 microns. Twenty parts of an aqueous solution containing 3% of sodium alginate as a dispersing agent are incorporated therein to obtain a suspension.

The dosage rate of the diphenyl sulfone compounds (I) may vary depending upon the application mode, applied crop plants or weeds, kind of composition, weather, etc. Generally, however, the dosage rate may be from 0.5 to 200 grams, preferably from 1 to 50 grams, of the active ingredient per are.

Besides, the diphenyl sulfone compounds (I) of the invention may be used together with other herbicides to improve their activity as herbicides, and in some cases, a synergistic effect can be expected. Examples of other herbicides include, for instance, phenoxy series herbicides such as 2,4-dichlorophenoxyacetic acid (2,4-D), 2-methyl-4-chlorophenoxyacetic acid (MCPA), 2-methyl-4-chlorophenoxybutyric acid (2,4-DB), 2-(2-methyl-4-chlorophenoxy)propionic acid (mecoprop), methyl 2-[4-(2,4-dichlorophenoxy)phenoxy]propionate (dichlohopmethyl), butyl 2-[4-(5-trifluoromethyl-2-pyridyloxy)phenoxy]propionate (fluadihopbutyl) and 2-[4-(3,5-dichloro-2-pyridyloxy)phenoxy]propionic acid (including their esters and salts); diphenyl ether series herbicides such as 2,4-dichlorophenyl-4'-nitrophenyl ether (nitrofen), 2,4,6-trichlorophenyl-4'-nitrophenyl ether (chloronitrofen), 2-chloro-4-trifluoromethylphenyl-3'-ethoxy-4'-nitrophenyl ether (oxyfluorofen), 2,4-dichlorophenyl-4'-nitro-3'-methoxyphenyl ether (chloromethoxynyl), 2,4-dichlorophenyl-3'-methoxycarbonyl-4'-nitrophenyl ether (biphenox) and 5-[2-chloro-4-(trifluoromethyl)phenoxy]-2-nitrobenzoic acid (acyfluorofen); triazine series herbicides such as 2-chloro-4,6-bisethylamino-1,3,5-triazine (simazine), 2-chloro-4-ethylamino-6-isopropylamino-1,3,5-triazine (atrazine), 2-methylthio-4,6-bisethylamino-1,3,5-triazine (simetryn), 2-methylthio-4,6-bisisopropylamino-1,3,5-triazine (prometryn), 2-chloro-4,6-bisisopropylamino-1,3,5-triazine (propazine), 2-(2-chloro-4-ethylamino-s-triazin-6-ylamino)-2-methylpropionitrile (cyanazine), 4-amino-6-t-butyl-3-methylthio-1,2,4-triazine-5(4H)-one (metripzine), 3-cyclohexyl-6-dimethylamino-1-methyl-s-triazine-2,4-dione (hexadinon), 2-methylthio-4-ethylamino-6-isopropylamino-1,3,5-triazine (ametryn), 2-methylthio-4-(1,2,-dimethylpropylamino)-6-ethylamino-1,3,5-triazine (dimethametryn) and 4-amino-3-methyl-6-phenyl-1,2,4-triazin-5(4H)-one (methamitron); urea series herbicides such as 3-(3,4-dichlorophenyl)-1,1-dimethylurea (diuron), 3-(3,4dichlorophenyl)-1-methoxy-1-methylurea (linuron), 1-(2,2-dimethylbenzyl)-3-p-tolylurea (dymron), 1,1-dimethyl-3-(3-trifluoromethylphenyl)urea (fluometuron), 3-(4-bromo-3-chlorophenyl)-1-methoxy-1-methylurea (chlorobromron); 3-[4-(4-chlorophenoxy)-phenyl]-1,1-dimethylurea (chloroxuron), 3-(4-isopropylphenyl)-1,1-dimethylurea (isoproturon), 3-(2-benzothiazolyl)-1,3-dimethylurea (methabenzthiazuron), 3-(5-t-butyl-3,4-thiadiazol-2-yl)-4-hydroxy-1-methyl-2-imidazolidone (butydazole) and 3-(3-chloro-4methoxyphenyl)-1,1-dimethylurea (methochlosuron); carbamate series herbicides such as isopropyl-N-(3-chlorophenyl)carbamate (chloropropham), methyl-N-(3,4-dichlorophenyl)carbamate (swep), 4-chloro-2-butynyl-N-(3-chlorophenyl)carbamate (barban), 3-(methoxycarbonylamino)phenyl-N-(3-methylphenyl)carbamate (phenmedipham), methyl-N-(4-aminobenzenesulfonyl)carbamate (asulam) and 3-isopropoxycarbonylaminophenyl-N-ethylcarbanilate (phenisopham); thiolcarbamate series herbicides such as s-(4-chlorobenzyl)-N,N-diethylthiocarbamate (benthiocarb), s-ethyl-N,N-hexamethylenethiolcarbamate (molinate), s-ethyl-N,N-di-n-propylthiolcarbamate (EPTC), s-ethyl-N,N- diisobutylthiolcarbamate (butylate), s-n-propyl-N,N-di-n-propylthiolcarbamate (vernolate), s-2,3,3-trichloroallyl-N,N-diisopropylthiolcarbamate (trialate), s-ethyl-N-ethyl-N-cyclohexylthiolcarbamate (cycloate) and s-(3-chlorobenzyl)-N,N-di-sec-butylthiolcarbamate (thiocarbazyl); amide series herbicides such as 3,4-dichloropropionanilide (propanyl), N-methoxymethyl-2,6-diethyl-α-chloroacetanilide (alachlor), 2-chloro-2',6'-diethyl-N-(butoxymethyl)acetanilide (butachlor), 2-chloro-N-(2-ethyl-6-methylphenyl)-N-(2-methoxy-1-methylethyl)acetamide (methorachlor), N-chloroacetyl-N-(2,6-diethylphenyl)glycinethyl ester (diethatyl), 2-chloro-N-isopropylacetanilide (propachlor), N,N-dimethyl-2,2-diphenylacetamide (diphenamid), N-naphthylphthalamic acid (naphthalam), N-(1,1-dimethylpropynyl)-3,5-dichlorobenzamide (pronamide), ethyl N-benzoyl-N-(3,4-dichlorophenyl)-2-aminopropionate (benzoylprop), methyl-N-benzoyl-N-(3-chloro-4-fluorophenyl)-2-aminopropionate (phramprop) and 5'-(trifluoromethanesulfonamido)acet-2',4'-oxylide (mefluidide); uracil series herbicides such as 5-bromo-3-sec-butyl-6-methyluracil (bromacil), 3-cyclohexyl-5,6-trimethyleneuracil (lenacil) and 3-t-5-chloro-6-methyluracil (terbacil); benzoic acid series herbicides such as 2,5dichloro-3-aminobenzoic acid (chloramben), 3,6-dichloro-2-methoxybenzoic acid (dicamba) and dimethyltetrachloroterephthalate (DCPA); phosphorus series herbicides such as N,N-bis(phosphonomethyl)glycine (glyphosate), O-ethyl-O-(2-nitro-5-methylphenyl)-N-sec-butylphosphoramidothioate (butamifos), s-(2-methyl-1-piperidylcarbonylmethyl) O,O-di-n-propyldithiophosphate (piperofos) and O,O-diisopropyl-s-(2benzenesulfonylaminoethyl)phosphorodithioate (bensulide); toluidine series herbicides such as α,α,α-trifluoro-2,6-dinitro-N,N-dipropyl-p-toluidine (trifluralin), 3,4-dimethyl-2,6-dinitro-N-1-ethylpropylanilide (pendimethalin), α,α,α-trifluoro-2,6dinitro-N-propyl-N-cyclopropyl-p-toluidine (profluoraline) and 4-(methylsulfonyl)-2,6-dinitro-N,N-dipropylaniline (nitralin); arsenic acid series herbicides such as disodium methanearsonate (DSMA) and monosodium methanearsonate (MSMA); diazine series herbicides such as maleic hydrazide (MH), 3-(2,4-dichloro-5-isopropoxyphenyl)-5-t-butyl-3,4-oxadiazol-2(3H)-one (oxadiazon), 2-(3',4'-dichlorophenyl)-4-methyltetrahydro-1,2,4-oxadiazole-3,5dione (methazole), 3-isopropyl-1H,2,1,3-benzothiadiazin-(4)-3H-one-2,2-dioxide (pentazon) and 4-(2,4-dichlorobenzoyl)-1,3-dimethylpyrazol-5-yl-p-toluenesulfonate (pyrazolate); pyridine series herbicides such as 4-amino-3,5,6-trichloropicolinic acid (picloram) and 1-methyl-3-phenyl-5-(3-trifluoromethylphenyl)pyridin-4(1H)-one (fuluridon); nitrile series herbicides such as 2,6-dichlorobenzonitrile (dichlobenil), 3,5-diiodo-4-hydroxybenzonitrile (anioxynil) and 3,5-dibromo-4-hydroxybenzonitrile (bromoxynil); fatty acid series herbicides such as 2,2-dichloropropionic acid (dalapon) and 2,2,3,3-tetrafluoropropionic acid (tetrapion) (including their salts); α-(β-naphthoxy)propionanilide (naproanilide); 1,2-dimethyl-3,5-diphenyl-1H-pyrazolium methysulfate (diphenzoquat), 2-methyl-4-phenylsulfonyltrifluoromethylsulfoanilide (perfluidon); 3-amino-1,2,4-triazole (amitorol); 4-chloro-5-methylamino-2-(3-trifluoromethylphenyl)pyridazin-3(2H)-one (norfluorazon); 2-sec-butyl-4,6-dinitrophenol (dinoseb); 2-ethoxy-2,3dihydro-3,3-dimethyl-5-benzofuranylmethanesulfonate (ethofumesate); 5-amino-4-chloro-2-phenylpyridazin-3(2)-one (pyrazon); 1,1'-dimethyl-4,4'-bipyridinium dichloride (paraquat); 1,1'-ethylene-2,2'-bipyridinium dibromide (diquat); 2-[1-(N-allyloxyamino)butylidene]-5,5-dimethyl-4-methoxycarbonylcyclohexane-1,3-dione sodium salt (alloxydimsodium); 2-(N-ethoxybutylidyl)-5-(2-ethylpropyl)-3-hydroxy-2-cyclohexen-1-one; 2-chloro-N-[(4-methoxy-6-methyl-1,3,5-triazin-2-yl)aminocarbonyl]benzenesulfonamide (chlorosulfuron), etc.

When desired, the diphenyl sulfone compounds (I) may be applied in combination with indesticides, nematocides, fungicides, plant growth regulators, fertilizers, etc.

The application of the diphenyl sulfone compounds (I) as herbicides will be illustratively shown in the following Examples wherein the phytotoxicity to crop plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity and the herbicidal activity were evaluated by the standard given in the table below.

| Rating value | Fresh weight (percentage to untreated plot) (%) | |
|---|---|---|
| | Herbicidal activity | Phytotoxicity |
| 0 | 91– | 91– |
| 1 | 71–90 | 71–90 |
| 2 | 41–70 | 51–70 |
| 3 | 11–40 | 31–50 |
| 4 | 1–10 | 11–30 |
| 5 | 0 | 0–10 |

TEST EXAMPLE 1

Cylindrical plastic pots (diameter, 10 cm; height, 10 cm) were filled with upland field soil, and the seeds of barnyardgrass, wild oat, radish and velvetleaf were sowed therein and grown for 10 days in a greenhouse. A designed amount of the test compound formulated into an emulsifiable concentrate and dispersed in water (including a spreading agent) was sprayed to the test plants over the top by means of a small hand sprayer at a spray volume of 10 liters per are. Thereafter, the test plants were grown for 20 days in the greenhouse, and herbicidal activity was examined. The results are shown in Table 2.

TABLE 2

| Compound No. | Dosage (weight of active ingredient, g/are) | Herbicidal activity | | | |
|---|---|---|---|---|---|
| | | Barnyard grass | Wild oat | Radish | Velvetleaf |
| 1 | 40 | 4 | 4 | 5 | 5 |
| | 10 | 4 | 4 | 5 | 5 |
| 2 | 40 | 5 | 1 | 5 | 5 |
| | 10 | 3 | 0 | 5 | 5 |
| 3 | 40 | 4 | 5 | 5 | 5 |
| | 10 | 2 | 3 | 5 | 5 |
| 4 | 40 | 5 | 5 | 5 | 5 |
| | 10 | 4 | 4 | 5 | 5 |
| 5 | 40 | 4 | 5 | 5 | 5 |
| | 10 | 3 | 2 | 5 | 5 |
| 6 | 40 | 4 | 4 | 5 | 5 |
| | 10 | 3 | 1 | 5 | 5 |
| 7 | 40 | 5 | 5 | 5 | 5 |
| | 10 | 4 | 3 | 5 | 5 |
| 8 | 40 | 5 | 5 | 5 | 5 |
| | 10 | 4 | 3 | 5 | 5 |
| 9 | 40 | 4 | 3 | 5 | 5 |
| | 10 | 3 | 1 | 5 | 5 |

TABLE 2-continued

| Compound No. | Dosage (weight of active ingredient, g/are) | Herbicidal activity | | | |
|---|---|---|---|---|---|
| | | Barnyard grass | Wild oat | Radish | Velvetleaf |
| 10 | 40 | 5 | 5 | 5 | 5 |
| | 10 | 5 | 5 | 5 | 5 |
| 11 | 40 | 5 | 5 | 5 | 5 |
| | 10 | 2 | 4 | 5 | 5 |
| 12 | 40 | 5 | 5 | 5 | 5 |
| | 10 | 4 | 3 | 5 | 5 |
| 13 | 40 | 5 | 3 | 5 | 5 |
| | 10 | 3 | 2 | 5 | 5 |
| 14 | 40 | 4 | 4 | 5 | 5 |
| | 10 | 3 | 3 | 5 | 5 |
| 15 | 40 | 4 | 2 | 5 | 5 |
| 16 | 40 | 5 | 5 | 5 | 5 |
| | 10 | 5 | 3 | 5 | 5 |
| 17 | 40 | 5 | 5 | 5 | 5 |
| | 10 | 4 | 3 | 5 | 5 |
| 18 | 40 | 4 | 2 | 5 | 5 |
| | 10 | 3 | 1 | 5 | 5 |
| 19 | 40 | 5 | 3 | 5 | 5 |
| | 10 | 5 | 1 | 5 | 5 |
| 20 | 40 | 5 | 2 | 5 | 5 |
| | 10 | 3 | 1 | 5 | 5 |
| 21 | 40 | 5 | 5 | 5 | 5 |
| | 10 | 4 | 1 | 5 | 5 |
| 22 | 40 | 5 | 5 | 5 | 5 |
| | 10 | 3 | 2 | 5 | 5 |
| 23 | 40 | 5 | 5 | 5 | 5 |
| | 10 | 2 | 3 | 5 | 5 |
| 24 | 40 | 4 | 5 | 5 | 5 |
| | 10 | 3 | 1 | 5 | 5 |
| 25 | 40 | 5 | 4 | 5 | 5 |
| | 10 | 2 | 2 | 5 | 5 |
| 26 | 40 | 3 | 1 | 5 | 5 |
| 27 | 40 | 5 | 5 | 5 | 5 |
| | 10 | 2 | 4 | 5 | 5 |
| 28 | 40 | 5 | 5 | 5 | 5 |
| | 10 | 4 | 5 | 5 | 5 |
| 29 | 40 | 5 | 5 | 5 | 5 |
| | 10 | 4 | 5 | 5 | 5 |
| 30 | 40 | 5 | 2 | 5 | 5 |
| | 10 | 4 | 1 | 5 | 5 |
| 31 | 40 | 4 | 3 | 5 | 5 |
| | 10 | 3 | 1 | 5 | 5 |
| 32 | 40 | 5 | 5 | 5 | 5 |
| | 10 | 3 | 1 | 5 | 5 |
| 33 | 40 | 5 | 5 | 5 | 5 |
| | 10 | 3 | 2 | 5 | 5 |
| 34 | 40 | 2 | 1 | 5 | 5 |
| 35 | 40 | 3 | 2 | 5 | 5 |
| 36 | 40 | 4 | 3 | 5 | 5 |
| 37 | 40 | 5 | 4 | 5 | 5 |
| | 10 | 3 | 2 | 5 | 5 |
| 38 | 40 | 3 | 3 | 5 | 5 |
| 39 | 40 | 5 | 5 | 5 | 5 |
| | 10 | 3 | 2 | 5 | 5 |
| 40 | 40 | 5 | 5 | 5 | 5 |
| | 10 | 4 | 4 | 5 | 5 |
| 41 | 40 | 5 | 5 | 5 | 5 |
| | 10 | 4 | 3 | 5 | 5 |
| 42 | 40 | 5 | 5 | 5 | 5 |
| | 10 | 3 | 4 | 5 | 5 |
| 43 | 40 | 5 | 4 | 5 | 5 |
| | 10 | 3 | 2 | 5 | 5 |
| 44 | 40 | 5 | 5 | 5 | 5 |
| | 10 | 3 | 3 | 5 | 5 |
| 45 | 40 | 5 | 5 | 5 | 5 |
| | 10 | 4 | 4 | 5 | 5 |
| 46 | 40 | 5 | 5 | 5 | 5 |
| | 10 | 4 | 3 | 5 | 5 |
| 47 | 40 | 5 | 5 | 5 | 5 |
| | 10 | 3 | 3 | 5 | 3 |
| 48 | 40 | 5 | 5 | 5 | 5 |
| | 10 | 2 | 3 | 5 | 5 |
| 49 | 40 | 5 | 5 | 5 | 5 |
| | 10 | 3 | 2 | 5 | 5 |
| 50 | 40 | 5 | 5 | 5 | 5 |
| | 10 | 3 | 3 | 5 | 5 |
| 51 | 40 | 5 | 5 | 5 | 5 |
| | 10 | 2 | 3 | 5 | 5 |
| 52 | 40 | 5 | 5 | 5 | 5 |
| | 10 | 5 | 3 | 5 | 5 |
| 53 | 40 | 5 | 5 | 5 | 5 |
| | 10 | 5 | 2 | 5 | 5 |
| 54 | 40 | 5 | 5 | 5 | 5 |
| | 10 | 3 | 4 | 5 | 5 |
| 55 | 40 | 5 | 5 | 5 | 5 |
| | 10 | 3 | 3 | 5 | 5 |
| 56 | 40 | 5 | 5 | 5 | 5 |
| | 10 | 5 | 4 | 5 | 5 |
| 57 | 40 | 5 | 5 | 5 | 5 |
| | 10 | 4 | 4 | 5 | 5 |
| 58 | 40 | 5 | 5 | 5 | 5 |
| | 10 | 4 | 3 | 5 | 5 |
| 59 | 40 | 5 | 5 | 5 | 5 |
| | 10 | 3 | 4 | 5 | 5 |
| 60 | 40 | 5 | 5 | 5 | 5 |
| | 10 | 3 | 3 | 5 | 5 |
| 61 | 40 | 5 | 5 | 5 | 5 |
| | 10 | 4 | 4 | 5 | 5 |
| 62 | 40 | 5 | 5 | 5 | 5 |
| | 10 | 5 | 4 | 5 | 5 |
| 63 | 40 | 5 | 5 | 5 | 5 |
| | 10 | 4 | 3 | 5 | 5 |
| 64 | 40 | 5 | 5 | 5 | 5 |
| | 10 | 5 | 4 | 5 | 5 |
| 65 | 40 | 5 | 5 | 5 | 5 |
| | 10 | 3 | 4 | 5 | 5 |
| 66 | 40 | 5 | 4 | 5 | 5 |
| 67 | 40 | 5 | 5 | 5 | 5 |
| | 10 | 5 | 3 | 5 | 5 |
| 68 | 40 | 5 | 5 | 5 | 5 |
| | 10 | 3 | 3 | 5 | 5 |
| 69 | 40 | 5 | 5 | 5 | 5 |
| | 10 | 4 | 3 | 5 | 5 |
| 70 | 40 | 5 | 5 | 5 | 5 |
| | 10 | 4 | 4 | 5 | 5 |
| 71 | 40 | 5 | 4 | 5 | 5 |
| | 10 | 3 | 3 | 5 | 5 |
| 72 | 40 | 5 | 5 | 5 | 5 |
| | 10 | 3 | 4 | 5 | 5 |
| 73 | 40 | 5 | 5 | 5 | 5 |
| | 10 | 4 | 4 | 5 | 5 |
| 74 | 40 | 5 | 5 | 5 | 5 |
| | 10 | 3 | 2 | 5 | 5 |
| 75 | 40 | 5 | 5 | 5 | 5 |
| | 10 | 2 | 4 | 5 | 5 |
| 76 | 40 | 4 | 4 | 5 | 5 |
| | 10 | 3 | 1 | 5 | 5 |
| 77 | 40 | 5 | 5 | 5 | 5 |
| 78 | 40 | 5 | 5 | 5 | 5 |
| | 10 | 4 | 4 | 5 | 5 |
| 79 | 40 | 5 | 3 | 5 | 5 |
| | 10 | 4 | 1 | 5 | 5 |
| 80 | 40 | 5 | 4 | 5 | 5 |
| | 10 | 3 | 1 | 5 | 5 |
| 81 | 40 | 2 | 4 | 5 | 5 |
| 82 | 40 | 4 | 5 | 5 | 5 |
| | 10 | 2 | 3 | 5 | 5 |
| 83 | 40 | 5 | 5 | 5 | 5 |
| | 10 | 3 | 2 | 5 | 5 |
| 84 | 40 | 2 | 3 | 5 | 5 |
| 85 | 40 | 5 | 5 | 5 | 5 |
| | 10 | 2 | 3 | 5 | 5 |
| 86 | 40 | 5 | 5 | 5 | 5 |
| 87 | 40 | 5 | 5 | 5 | 5 |
| 88 | 40 | 5 | 5 | 5 | 5 |
| | 10 | 4 | 4 | 5 | 5 |
| 89 | 40 | 5 | 5 | 5 | 5 |
| | 10 | 5 | 4 | 5 | 5 |
| 90 | 40 | 5 | 4 | 5 | 5 |
| 91 | 40 | 5 | 5 | 5 | 5 |
| | 10 | 5 | 5 | 5 | 5 |
| 92 | 40 | 5 | 5 | 5 | 5 |

TABLE 2-continued

| Compound No. | Dosage (weight of active ingredient, g/are) | Herbicidal activity | | | |
|---|---|---|---|---|---|
| | | Barnyard grass | Wild oat | Radish | Velvetleaf |
| 93 | 10 | 5 | 5 | 5 | 5 |
| | 40 | 5 | 5 | 5 | 5 |
| 94 | 40 | 5 | 5 | 5 | 5 |
| | 10 | 5 | 4 | 5 | 5 |
| 95 | 40 | 5 | 5 | 5 | 5 |
| | 10 | 5 | 3 | 5 | 5 |
| 96 | 40 | 5 | 5 | 5 | 5 |
| 97 | 40 | 5 | 5 | 5 | 5 |
| | 10 | 5 | 3 | 5 | 5 |
| 98 | 40 | 5 | 5 | 5 | 5 |
| | 10 | 5 | 3 | 5 | 5 |
| 99 | 40 | 5 | 3 | 5 | 5 |
| 100 | 40 | 5 | 5 | 5 | 5 |
| | 10 | 5 | 5 | 5 | 5 |
| 101 | 40 | 5 | 5 | 5 | 5 |
| | 10 | 5 | 3 | 5 | 5 |
| 102 | 40 | 5 | 4 | 5 | 5 |
| 103 | 40 | 5 | 5 | 5 | 5 |
| | 10 | 5 | 3 | 5 | 5 |
| 104 | 40 | 5 | 5 | 5 | 5 |
| | 10 | 4 | 4 | 5 | 5 |
| 105 | 40 | 4 | 4 | 5 | 5 |
| 106 | 40 | 4 | 4 | 5 | 5 |
| | 10 | 4 | 2 | 5 | 5 |
| 107 | 40 | 4 | 4 | 5 | 5 |
| | 10 | 4 | 2 | 5 | 5 |
| 108 | 40 | 5 | 3 | 5 | 5 |
| | 10 | 4 | 2 | 5 | 5 |
| 109 | 40 | 5 | 5 | 5 | 5 |
| | 10 | 4 | 3 | 5 | 5 |
| 110 | 40 | 5 | 5 | 5 | 5 |
| | 10 | 4 | 4 | 5 | 5 |
| 111 | 40 | 5 | 5 | 5 | 5 |
| | 10 | 4 | 4 | 5 | 5 |
| 112 | 40 | 5 | 4 | 5 | 5 |
| | 10 | 5 | 3 | 5 | 5 |
| 113 | 40 | 4 | 5 | 5 | 5 |
| | 10 | 3 | 4 | 5 | 5 |
| 114 | 40 | 5 | 5 | 5 | 5 |
| | 10 | 5 | 4 | 5 | 5 |
| 115 | 40 | 5 | 5 | 5 | 5 |
| | 10 | 5 | 5 | 5 | 5 |
| 116 | 40 | 5 | 5 | 5 | 5 |
| | 10 | 5 | 4 | 5 | 5 |
| 117 | 40 | 5 | 5 | 5 | 5 |
| | 10 | 5 | 3 | 5 | 5 |
| 118 | 40 | 5 | 5 | 5 | 5 |
| | 10 | 5 | 5 | 5 | 5 |
| 119 | 40 | 5 | 5 | 5 | 5 |
| | 10 | 5 | 4 | 5 | 5 |
| 120 | 40 | 4 | 3 | 5 | 5 |
| | 10 | 3 | 2 | 5 | 5 |
| 121 | 40 | 5 | 5 | 5 | 5 |
| | 10 | 5 | 4 | 5 | 5 |
| 122 | 40 | 5 | 4 | 5 | 5 |
| | 10 | 4 | 3 | 5 | 5 |
| 123 | 40 | 5 | 5 | 5 | 5 |
| | 10 | 5 | 3 | 5 | 5 |
| 124 | 40 | 5 | 3 | 5 | 5 |
| 125 | 40 | 5 | 5 | 5 | 5 |
| | 10 | 4 | 4 | 5 | 5 |
| 126 | 40 | 5 | 4 | 5 | 5 |
| | 10 | 4 | 2 | 5 | 5 |
| 127 | 40 | 5 | 4 | 5 | 5 |
| 129 | 40 | 3 | 2 | 4 | 5 |
| 130 | 40 | 3 | 2 | 5 | 5 |
| 131 | 40 | 3 | 2 | 5 | 5 |
| | 10 | 3 | 1 | 5 | 5 |
| 132 | 40 | 5 | 5 | 5 | 5 |
| | 10 | 4 | 1 | 5 | 5 |
| 133 | 40 | 3 | 1 | 5 | 5 |
| 134 | 40 | 5 | 5 | 5 | 5 |
| | 10 | 3 | 3 | 4 | 5 |
| 135 | 40 | 4 | 5 | 5 | 5 |
| | 10 | 3 | 3 | 5 | 5 |
| 136 | 40 | 4 | 5 | 5 | 5 |
| | 10 | 3 | 3 | 5 | 5 |
| 137 | 40 | 3 | 2 | 5 | 5 |
| 138 | 40 | 5 | 5 | 5 | 5 |
| | 10 | 4 | 3 | 5 | 5 |
| 139 | 40 | 5 | 5 | 5 | 5 |
| | 10 | 3 | 3 | 5 | 5 |
| 140 | 40 | 5 | 4 | 5 | 5 |
| | 10 | 4 | 3 | 5 | 5 |
| 141 | 40 | 3 | 2 | 5 | 5 |
| 142 | 40 | 5 | 5 | 5 | 5 |
| | 10 | 4 | 3 | 5 | 5 |
| 143 | 40 | 5 | 4 | 5 | 5 |
| | 10 | 4 | 2 | 5 | 5 |
| 144 | 40 | 5 | 5 | 5 | 5 |

TEST EXAMPLE 2

Plastic trays (35 cm×25 cm×10 cm) were filled with upland field soil, and the seeds of corn, wheat, soybean, sunflower, cocklebur, tall morningglory, hemp sesbania, velvetleaf, redroot pigweed, birdseye speedwell and black nightshade were sowed therein and grown for 3 weeks in a greenhouse. Every two trays were placed in a frame (50 cm×100 cm×40 cm) and a designed amount of the test compound was sprayed thereover by means of a small hand sprayer. The test plants were further grown for 3 weeks in the greenhouse and herbicidal activity and phytotoxicity were examined. The results are shown in Table 3. In this treatment, the test compound was formulated into an emulsifiable concentrate and applied by diluting it in water (25 liters) with the addition of a spreading agent. At the time of application, the plants were generally at the 1 to 4 leaf stage and in 1.5 to 15 cm height.

TABLE 3

| Compound No. | Dosage (weight of active ingredient, g/are) | Phytotoxicity | | | Herbicidal activity | | | | | | | |
|---|---|---|---|---|---|---|---|---|---|---|---|---|
| | | Corn | Wheat | Soybean | Sunflower | Cocklebur | Tall morningglory | Hemp sesbania | Velvetleaf | Redroot pigweed | Birdseye speedwell | Black nightshade |
| 2 | 5 | 1 | 0 | 1 | 5 | 5 | 5 | 5 | 5 | 5 | 5 | 5 |
| | 2.5 | 0 | 0 | 1 | 4 | 5 | 5 | 5 | 5 | 5 | 5 | 5 |
| 3 | 5 | 1 | 0 | — | 5 | 5 | 5 | 5 | 5 | 5 | 5 | 5 |
| | 2.5 | 0 | 0 | 1 | 5 | 5 | 5 | 5 | 5 | 5 | 4 | 5 |
| 4 | 5 | 0 | 1 | 1 | 5 | 5 | 5 | 5 | 5 | 5 | 5 | 5 |
| | 2.5 | 0 | 0 | 1 | 4 | 5 | 5 | 5 | 5 | 5 | 4 | 5 |
| 6 | 5 | — | 1 | — | 4 | 5 | 5 | 5 | 5 | 5 | 5 | 5 |
| | 2.5 | 0 | 0 | 1 | 4 | 5 | 5 | 4 | 5 | 5 | 4 | 5 |
| 8 | 5 | — | 1 | — | 5 | 5 | 5 | 5 | 5 | 5 | 5 | 5 |
| | 2.5 | 1 | 0 | — | 3 | 5 | 5 | 5 | 5 | 5 | 5 | 5 |

TABLE 3-continued

| Compound No. | Dosage (weight of active ingredient, g/are) | Phytotoxicity | | | Herbicidal activity | | | | | | | |
| --- | --- | --- | --- | --- | --- | --- | --- | --- | --- | --- | --- | --- |
| | | Corn | Wheat | Soybean | Sunflower | Cocklebur | Tall morningglory | Hemp sesbania | Velvetleaf | Redroot pigweed | Birdseye speedwell | Black nightshade |
| 10 | 2.5 | — | 0 | — | 5 | 5 | 5 | 5 | 5 | 5 | 5 | 5 |
| | 1.25 | 0 | 0 | 1 | 5 | 5 | 5 | 5 | 5 | 5 | 5 | 5 |
| 11 | 2.5 | — | 1 | — | 5 | 5 | 5 | 5 | 5 | 5 | 5 | 5 |
| | 1.25 | 1 | 0 | 1 | 5 | 5 | 5 | 5 | 5 | 5 | 4 | 5 |
| 14 | 5 | — | 1 | 1 | 5 | 5 | 5 | 5 | 5 | 5 | 5 | 5 |
| | 2.5 | 1 | 0 | 1 | 4 | 5 | 5 | 5 | 5 | 5 | 5 | 5 |
| 16 | 2.5 | — | 0 | — | 5 | 5 | 5 | 5 | 5 | 5 | 5 | 5 |
| | 1.25 | 1 | 0 | 1 | 4 | 5 | 5 | 5 | 5 | 5 | 4 | 5 |
| 17 | 2.5 | 1 | 1 | — | 5 | 5 | 5 | 5 | 5 | 5 | 5 | 5 |
| | 1.25 | 1 | 0 | 1 | 4 | 5 | 5 | 5 | 5 | 5 | 5 | 5 |
| 19 | 2.5 | 1 | 1 | — | 4 | 5 | 5 | 5 | 5 | 5 | 5 | 5 |
| | 1.25 | 0 | 0 | 1 | 3 | 5 | 5 | 5 | 5 | 5 | 4 | 5 |
| 20 | 2.5 | 1 | 0 | 1 | 4 | 5 | 5 | 5 | 5 | 5 | 5 | 5 |
| | 1.25 | 0 | 0 | 1 | 4 | 5 | 5 | 5 | 5 | 5 | 5 | 5 |
| 21 | 2.5 | 1 | 1 | — | 5 | 5 | 5 | 5 | 5 | 5 | 5 | 5 |
| | 1.25 | 0 | 0 | 1 | 3 | 5 | 5 | 5 | 5 | 5 | 4 | 5 |
| 22 | 5 | 1 | 0 | 1 | 5 | 5 | 5 | 5 | 5 | 5 | 5 | 5 |
| | 2.5 | 0 | 0 | 0 | 4 | 5 | 5 | 5 | 5 | 5 | 5 | 5 |
| 23 | 2.5 | 1 | 1 | — | 5 | 5 | 5 | 5 | 5 | 5 | 5 | 5 |
| | 1.25 | 0 | 0 | — | 4 | 5 | 5 | 5 | 5 | 5 | 4 | 5 |
| 24 | 5 | 1 | 1 | — | 5 | 5 | 5 | 5 | 5 | 5 | 5 | 5 |
| | 2.5 | 1 | 0 | 1 | 3 | 5 | 5 | 5 | 5 | 5 | 5 | 5 |
| 25 | 2.5 | — | 1 | — | 5 | 5 | 5 | 5 | 5 | 5 | 5 | 5 |
| | 1.25 | 0 | 0 | — | 5 | 5 | 5 | 5 | 5 | 5 | 3 | 5 |
| 27 | 5 | 1 | 0 | 1 | 5 | 5 | 5 | 5 | 5 | 5 | 5 | 5 |
| | 2.5 | 0 | 0 | 0 | 3 | 5 | 5 | 5 | 5 | 5 | 4 | 5 |
| 28 | 5 | — | 1 | — | 4 | 5 | 5 | 5 | 5 | 5 | 5 | 5 |
| | 2.5 | 0 | 1 | — | 3 | 4 | 5 | 5 | 5 | 5 | 5 | 5 |
| 29 | 5 | 1 | 1 | — | 5 | 5 | 5 | 5 | 5 | 5 | 5 | 5 |
| | 2.5 | 0 | 0 | 1 | 3 | 5 | 5 | 5 | 5 | 5 | 5 | 5 |
| 32 | 5 | — | 1 | 1 | 4 | 5 | 5 | 5 | 5 | 5 | 5 | 5 |
| | 2.5 | — | 0 | 0 | 2 | 5 | 5 | 5 | 5 | 5 | 2 | 5 |
| 33 | 5 | — | 0 | 1 | 4 | 5 | 5 | 5 | 5 | 5 | 5 | 5 |
| | 2.5 | 0 | 0 | 1 | 3 | 5 | 5 | 4 | 5 | 5 | 3 | 5 |
| 37 | 5 | — | 1 | — | 5 | 5 | 5 | 5 | 5 | 5 | 5 | 5 |
| | 2.5 | 1 | 0 | 1 | 3 | 5 | 5 | 5 | 5 | 5 | 4 | 5 |
| 40 | 2.5 | 1 | — | — | 5 | 5 | 5 | 5 | 5 | 5 | 5 | 5 |
| | 1.25 | 0 | 1 | 1 | 5 | 5 | 5 | 5 | 5 | 5 | 5 | 5 |
| 42 | 2.5 | 1 | 1 | — | 5 | 5 | 5 | 5 | 5 | 5 | 5 | 5 |
| | 1.25 | 0 | 0 | — | 5 | 5 | 5 | 5 | 5 | 5 | 5 | 5 |
| 43 | 2.5 | — | 0 | — | 5 | 5 | 5 | 5 | 5 | 5 | 5 | 5 |
| | 1.25 | 1 | 0 | 1 | 4 | 5 | 5 | 5 | 5 | 5 | 5 | 5 |
| 44 | 5 | — | 1 | — | 5 | 5 | 5 | 5 | 5 | 5 | 5 | 5 |
| | 2.5 | 1 | 0 | 1 | 4 | 5 | 5 | 5 | 5 | 5 | 5 | 5 |
| 45 | 2.5 | — | 1 | — | 5 | 5 | 5 | 5 | 5 | 5 | 5 | 5 |
| | 1.25 | — | 0 | 1 | 5 | 5 | 5 | 5 | 5 | 5 | 5 | 5 |
| 47 | 2.5 | — | 1 | — | 5 | 5 | 5 | 5 | 5 | 5 | 5 | 5 |
| | 1.25 | 1 | 0 | 1 | 4 | 5 | 5 | 5 | 5 | 5 | 4 | 5 |
| 49 | 2.5 | 1 | — | — | 5 | 5 | 5 | 5 | 5 | 5 | 5 | 5 |
| | 1.25 | 0 | 1 | — | 4 | 5 | 5 | 5 | 5 | 5 | 5 | 5 |
| 51 | 2.5 | 1 | — | — | 5 | 5 | 5 | 5 | 5 | 5 | 5 | 5 |
| | 1.25 | 0 | 1 | 1 | 5 | 5 | 5 | 5 | 5 | 5 | 5 | 5 |
| 52 | 1.25 | 1 | 1 | — | 5 | 5 | 5 | 5 | 5 | 5 | 5 | 5 |
| | 0.63 | 0 | 0 | — | 5 | 5 | 5 | 5 | 5 | 5 | 5 | 5 |
| 53 | 1.25 | — | 1 | — | 5 | 5 | 5 | 5 | 5 | 5 | 5 | 5 |
| | 0.63 | — | 1 | 1 | 5 | 5 | 5 | 5 | 5 | 5 | 5 | 5 |
| 54 | 2.5 | — | 1 | — | 5 | 5 | 5 | 5 | 5 | 5 | 5 | 5 |
| | 1.25 | — | 0 | — | 5 | 5 | 5 | 5 | 5 | 5 | 5 | 5 |
| 55 | 2.5 | — | — | — | 5 | 5 | 5 | 5 | 5 | 5 | 5 | 5 |
| | 1.25 | 1 | 1 | — | 5 | 4 | 5 | 5 | 5 | 5 | 5 | 5 |
| 56 | 1.25 | 1 | 1 | — | 5 | 5 | 5 | 5 | 5 | 5 | 5 | 5 |
| | 0.63 | 0 | 1 | — | 5 | 5 | 5 | 5 | 5 | 5 | 5 | 5 |
| 58 | 2.5 | — | — | — | 5 | 5 | 5 | 5 | 5 | 5 | 5 | 5 |
| | 1.25 | — | 1 | — | 5 | 5 | 5 | 5 | 5 | 5 | 4 | 5 |
| 59 | 2.5 | — | — | — | 5 | 5 | 5 | 5 | 5 | 5 | 5 | 5 |
| | 1.25 | 1 | 1 | 1 | 5 | 5 | 5 | 5 | 5 | 5 | 5 | 5 |
| 61 | 2.5 | 1 | — | — | 5 | 5 | 5 | 5 | 5 | 5 | 5 | 5 |
| | 1.25 | 1 | 1 | 1 | 5 | 5 | 5 | 5 | 5 | 5 | 5 | 5 |
| 68 | 2.5 | — | 1 | — | 5 | 5 | 5 | 5 | 5 | 5 | 5 | 5 |
| | 1.25 | 1 | 0 | 1 | 4 | 5 | 5 | 5 | 5 | 5 | 4 | 5 |
| 69 | 2.5 | 1 | — | — | 5 | 5 | 5 | 5 | 5 | 5 | 5 | 5 |
| | 1.25 | 0 | 1 | — | 5 | 5 | 5 | 5 | 5 | 5 | 5 | 5 |
| 75 | 2.5 | 1 | 1 | — | 5 | 5 | 5 | 5 | 5 | 5 | 5 | 5 |
| | 1.25 | 0 | 1 | — | 5 | 5 | 5 | 5 | 5 | 5 | 5 | 5 |
| 76 | 2.5 | — | 1 | — | 5 | 5 | 5 | 5 | 5 | 5 | 5 | 5 |
| | 1.25 | — | 1 | — | 5 | 5 | 5 | 5 | 5 | 5 | 5 | 5 |

TABLE 3-continued

| Compound No. | Dosage (weight of active ingredient, g/are) | Phytotoxicity | | | Herbicidal activity | | | | | | | |
|---|---|---|---|---|---|---|---|---|---|---|---|---|
| | | Corn | Wheat | Soybean | Sunflower | Cocklebur | Tall morningglory | Hemp sesbania | Velvetleaf | Redroot pigweed | Birdseye speedwell | Black nightshade |
| 77 | 2.5 | — | 1 | 2 | 5 | 5 | 5 | 5 | 5 | 5 | 5 | 5 |
| | 1.25 | — | 0 | 1 | 5 | 5 | 5 | 5 | 5 | 5 | 5 | 5 |
| 80 | 2.5 | — | 0 | — | 5 | 5 | 5 | 5 | 5 | 5 | 5 | 5 |
| | 1.25 | — | 0 | — | 5 | 4 | 5 | 5 | 5 | 5 | 5 | 5 |
| 84 | 2.5 | 1 | 1 | — | 5 | 5 | 5 | 5 | 5 | 5 | 5 | 5 |
| | 1.25 | 1 | 0 | — | 4 | 4 | 5 | 5 | 5 | 5 | 5 | 4 |
| 96 | 2.5 | 1 | 1 | — | 5 | 5 | 5 | 5 | 5 | 5 | 5 | 5 |
| | 1.25 | 0 | 1 | 1 | 4 | 4 | 5 | 5 | 5 | 5 | 5 | 5 |
| 98 | 2.5 | 1 | — | — | 5 | 5 | 5 | 5 | 5 | 5 | 5 | 5 |
| | 1.25 | 1 | 1 | 1 | 5 | 5 | 5 | 5 | 5 | 5 | 5 | 5 |
| 107 | 2.5 | 2 | 1 | — | 5 | 5 | 5 | 5 | 5 | 5 | — | 5 |
| | 1.25 | 1 | 0 | 1 | 5 | 4 | 5 | 5 | 5 | 5 | — | 5 |
| 110 | 2.5 | 2 | 1 | — | 5 | 5 | 5 | — | 5 | 5 | — | 5 |
| | 1.25 | 1 | 0 | 1 | 5 | — | 5 | — | 5 | 5 | — | — |
| 111 | 2.5 | — | 0 | — | 5 | 5 | 5 | — | 5 | 5 | — | 4 |
| | 1.25 | — | 0 | — | 4 | 5 | 5 | — | 5 | 4 | — | — |
| 112 | 2.5 | — | 1 | — | 4 | 5 | 5 | — | 5 | 5 | — | 5 |
| | 1.25 | 1 | 0 | — | — | — | — | — | 5 | 5 | — | — |
| 113 | 2.5 | — | 1 | — | 5 | 5 | 5 | — | 5 | 5 | — | 3 |
| | 1.25 | 1 | 1 | — | — | 5 | 5 | — | 5 | 4 | — | — |
| 114 | 2.5 | — | 1 | — | 5 | 5 | 5 | — | 5 | 5 | — | 5 |
| | 1.25 | 1 | 0 | — | 3 | 3 | 5 | — | 5 | 5 | — | 5 |
| 115 | 2.5 | — | 2 | — | 5 | 5 | 5 | — | 5 | 5 | — | 5 |
| | 1.25 | 1 | 1 | — | 3 | 5 | 5 | — | 5 | 5 | — | — |
| 116 | 2.5 | — | 1 | — | 5 | 5 | 5 | — | 5 | 5 | — | 5 |
| | 1.25 | 1 | 1 | — | — | 5 | 5 | — | 5 | 5 | — | — |
| 117 | 2.5 | — | 1 | — | 5 | 5 | 5 | — | 5 | 5 | — | 5 |
| | 1.25 | — | 0 | — | 3 | 5 | 5 | — | — | 5 | — | — |
| 118 | 2.5 | — | 1 | — | 5 | 5 | 5 | — | 5 | 5 | — | 4 |
| | 1.25 | — | 1 | — | 5 | 5 | 5 | — | 5 | 5 | — | 4 |
| 119 | 2.5 | — | 1 | — | 4 | 5 | 5 | — | 5 | 5 | — | — |
| | 1.25 | — | 1 | — | 3 | 5 | 5 | — | 5 | 5 | — | — |
| 121 | 2.5 | — | 1 | — | 5 | 5 | 5 | — | 5 | 4 | — | — |
| | 1.25 | 1 | 1 | — | 3 | 5 | 5 | — | 5 | — | — | — |
| 122 | 2.5 | — | 1 | — | 5 | 5 | 5 | — | 5 | 5 | — | 4 |
| | 1.25 | 1 | 1 | — | 4 | — | 5 | — | 5 | 5 | — | — |
| 125 | 2.5 | — | 0 | — | 4 | 5 | 5 | — | 5 | 5 | — | — |
| | 1.25 | 1 | 0 | — | 3 | — | 5 | — | 5 | 5 | — | — |
| Acyfluorofen sodium* | 5 | 4 | 3 | 3 | 5 | 5 | 5 | 5 | 4 | 5 | 5 | 5 |
| | 2.5 | 2 | 1 | 2 | 3 | 4 | 5 | 5 | 3 | 5 | 5 | 5 |

Note:
*Commercially available herbicide having the following formula:

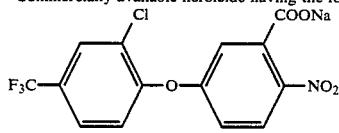

TEST EXAMPLE 3

Cylindrical plastic pots (diameter, 10 cm; height, 10 cm) were filled with upland field soil, and the seeds of barnyardgrass, wild oat, tall morningglory and velvetleaf as well as soybean were sowed therein. A designed amount of the test compound formulated into an emulsifiable concentrate and dispersed in water was sprayed over the soil by means of a small hand sprayer at a spray volume of 10 liters per are and the soil was mixed well at the depth of 4 cm from the surface. The test plants were grown for 20 days in a greenhouse, and herbicidal activity and phytotoxicity were examined. The results are shown in Table 4.

TABLE 4

| Compound No. | Dosage (weight of active ingredient, g/are) | Phytotoxicity Soybean | Herbicidal activity | | | |
|---|---|---|---|---|---|---|
| | | | Barnyardgrass | Wild oat | Tall morningglory | Velvetleaf |
| 2 | 80 | 1 | 3 | 0 | 5 | 5 |
| 3 | 80 | 1 | 4 | 2 | 5 | 5 |
| | 40 | 0 | 3 | 1 | 5 | 5 |
| 8 | 80 | 0 | 1 | 3 | 5 | 5 |
| 10 | 80 | 0 | 4 | 0 | 5 | 5 |
| 11 | 80 | 0 | 4 | 3 | 5 | 5 |
| | 40 | 0 | 2 | 2 | 5 | 5 |
| 15 | 80 | 1 | 0 | 0 | 5 | 5 |
| 16 | 80 | 0 | 3 | 2 | 5 | 5 |
| | 40 | 0 | 2 | 1 | 5 | 5 |
| 17 | 80 | 1 | 0 | 0 | 5 | 5 |
| 18 | 80 | 0 | 0 | 0 | 5 | 5 |
| 19 | 80 | 0 | 0 | 0 | 5 | 5 |
| 20 | 80 | 0 | 0 | 0 | 5 | 5 |
| | 40 | 0 | 0 | 0 | 5 | 5 |
| 21 | 80 | 0 | 3 | 1 | 5 | 5 |
| | 40 | 0 | 0 | 0 | 5 | 5 |

TABLE 4-continued

| Compound No. | Dosage (weight of active ingredient, g/are) | Phytotoxicity Soybean | Herbicidal activity Barnyardgrass | Wild oat | Tall morningglory | Velvetleaf |
|---|---|---|---|---|---|---|
| 23 | 80 | 1 | 3 | 0 | 5 | 5 |
|  | 40 | 0 | 2 | 0 | 5 | 5 |
| 25 | 80 | — | 2 | 0 | 5 | 5 |
| 27 | 80 | 0 | 1 | 0 | 5 | 5 |
| 28 | 80 | 0 | 0 | 2 | 5 | 5 |
| 29 | 80 | 0 | 3 | 0 | 5 | 5 |
| 31 | 80 | 1 | 3 | 3 | 5 | 5 |
|  | 40 | 0 | 2 | 1 | 5 | 5 |
| 32 | 80 | 1 | 3 | 0 | 5 | 5 |
| 33 | 80 | 1 | 4 | 0 | 5 | 5 |
|  | 40 | 0 | 3 | 0 | 5 | 5 |
| 36 | 80 | 1 | 3 | 3 | 5 | 5 |
| 39 | 80 | — | 4 | 0 | 5 | 5 |
| 40 | 80 | 1 | 3 | 1 | 5 | 5 |
| 41 | 80 | 1 | 3 | 1 | 5 | 5 |
| 42 | 80 | 0 | 1 | 0 | 4 | 5 |
| 43 | 80 | 0 | 0 | 0 | 4 | 5 |
| 44 | 40 | 1 | 3 | 1 | 5 | 5 |
| 45 | 80 | — | 3 | 2 | 5 | 5 |
| 46 | 80 | — | 3 | 3 | 5 | 5 |
| 47 | 40 | 1 | 3 | 0 | 4 | 5 |
| 48 | 40 | 1 | 3 | 1 | 4 | 5 |
| 49 | 40 | — | 4 | 2 | 5 | 5 |
| 50 | 40 | — | 3 | 1 | 5 | 5 |
| 51 | 80 | 1 | 4 | 1 | 5 | 5 |
| 52 | 40 | — | 2 | 0 | 5 | 5 |
| 53 | 80 | 1 | 3 | 0 | 5 | 5 |
| 54 | 20 | 0 | 1 | 0 | 5 | 5 |
| 55 | 20 | 0 | 3 | 0 | 4 | 5 |
| 56 | 20 | 0 | 2 | 0 | 5 | 5 |
| 58 | 80 | 0 | 4 | 1 | 5 | 5 |
| 59 | 20 | 0 | 0 | 0 | 5 | 5 |
| 62 | 80 | 0 | 2 | 1 | 5 | 5 |
| 63 | 80 | 0 | 3 | 2 | 5 | 5 |
|  | 20 | 0 | 0 | 0 | 5 | 5 |
| 64 | 80 | 0 | 0 | 0 | 5 | 5 |
| 65 | 80 | 0 | 0 | 0 | 5 | 5 |
| 66 | 80 | 0 | 0 | 0 | 5 | 5 |
| 67 | 80 | 0 | 3 | 3 | 5 | 5 |
| 68 | 80 | 1 | 4 | 2 | 5 | 5 |
| 69 | 80 | 0 | 0 | 0 | 5 | 5 |
| 71 | 80 | 0 | 0 | 0 | 5 | 5 |
| 72 | 80 | 0 | 0 | 0 | 5 | 5 |
| 73 | 80 | — | 4 | 3 | 5 | 5 |
| 74 | 80 | — | 3 | 3 | 5 | 5 |
| 75 | 80 | — | 4 | 2 | 5 | 5 |
| 76 | 80 | 1 | 1 | 1 | 5 | 5 |
| 77 | 80 | 0 | 3 | 0 | 5 | 5 |
| 82 | 80 | 1 | 3 | 0 | 5 | 5 |
| 83 | 80 | 0 | 2 | 0 | 5 | 5 |
| 84 | 80 | 0 | 1 | 0 | 5 | 5 |
| 88 | 80 | 0 | 0 | 0 | 5 | 5 |
| 91 | 20 | 1 | 2 | 0 | 5 | 5 |
| 100 | 20 | 0 | 0 | 0 | 5 | 5 |
| 105 | 80 | 0 | 4 | 2 | 5 | 5 |
| 107 | 80 | 0 | 5 | 2 | 5 | 5 |
|  | 20 | 0 | 4 | 0 | 5 | 5 |
| 108 | 80 | 1 | 4 | 1 | 5 | 5 |
|  | 20 | 0 | 2 | 0 | 5 | 5 |
| 109 | 80 | 0 | 4 | 1 | 5 | 5 |
| 110 | 80 | 0 | 4 | 2 | 4 | 5 |
| 111 | 80 | 0 | 3 | 2 | 5 | 5 |
|  | 20 | 0 | 0 | 0 | 5 | 5 |
| 112 | 80 | 0 | 3 | 2 | 5 | 5 |
|  | 20 | 0 | 0 | 0 | 5 | 5 |
| 113 | 80 | 0 | 3 | 2 | 5 | 5 |
|  | 20 | 0 | 0 | 0 | 5 | 5 |
| 114 | 80 | 0 | 4 | 2 | 5 | 5 |
|  | 20 | 0 | 0 | 0 | 5 | 5 |
| 115 | 80 | 0 | 4 | 3 | 5 | 5 |
|  | 20 | 0 | 2 | 0 | 5 | 5 |
| 116 | 80 | 0 | 4 | 3 | 5 | 5 |
|  | 20 | 0 | 3 | 0 | 5 | 5 |
| 117 | 80 | 0 | 4 | 2 | 5 | 5 |
|  | 20 | 0 | 3 | 0 | 5 | 5 |
| 118 | 80 | 0 | 4 | 0 | 5 | 5 |
|  | 20 | 0 | 3 | 0 | 5 | 5 |
| 119 | 80 | 0 | 3 | 0 | 5 | 5 |
|  | 20 | 0 | 2 | 0 | 5 | 5 |
| 120 | 80 | 0 | 3 | 2 | 5 | 5 |
|  | 20 | 0 | 2 | 2 | 5 | 5 |
| 121 | 80 | 0 | 4 | 2 | 5 | 5 |
|  | 20 | 0 | 4 | 2 | 5 | 5 |
| 122 | 80 | 0 | 4 | 2 | 5 | 5 |
|  | 20 | 0 | 3 | 0 | 5 | 5 |
| 123 | 80 | 0 | 4 | 2 | 5 | 5 |
|  | 20 | 0 | 3 | 0 | 5 | 5 |
| 125 | 80 | 0 | 3 | 0 | 5 | 5 |
|  | 20 | 0 | 2 | 0 | 5 | 5 |
| 126 | 80 | 0 | 3 | 2 | 5 | 5 |
|  | 20 | 0 | 0 | 0 | 5 | 5 |
| 129 | 80 | 0 | 0 | 0 | 4 | 5 |
| 130 | 80 | 0 | 2 | 2 | 5 | 5 |
| 131 | 80 | 0 | 3 | 2 | 5 | 5 |
|  | 20 | 0 | 0 | 0 | 5 | 5 |
| 132 | 80 | 0 | 3 | 2 | 5 | 5 |
|  | 20 | 0 | 0 | 0 | 5 | 5 |
| 133 | 80 | 0 | 2 | 2 | 5 | 5 |
|  | 20 | 0 | 0 | 0 | 4 | 5 |
| 134 | 80 | 0 | 2 | 2 | 5 | 5 |
| 135 | 80 | 0 | 3 | 2 | 5 | 5 |
|  | 20 | 0 | 0 | 0 | 4 | 5 |
| 136 | 80 | 0 | 4 | 2 | 5 | 5 |
|  | 20 | 0 | 0 | 0 | 4 | 5 |
| 138 | 80 | 0 | 3 | 2 | 5 | 5 |
|  | 20 | 0 | 1 | 1 | 5 | 5 |
| 139 | 80 | 0 | 3 | 2 | 5 | 5 |
|  | 20 | 0 | 0 | 0 | 5 | 5 |
| 140 | 80 | 0 | 2 | 2 | 5 | 5 |
|  | 20 | 0 | 0 | 0 | 5 | 5 |
| 142 | 80 | 0 | 3 | 2 | 5 | 5 |
|  | 20 | 0 | 0 | 0 | 5 | 5 |
| 143 | 80 | 0 | 2 | 2 | 5 | 5 |
|  | 20 | 0 | 0 | 0 | 5 | 5 |
| 144 | 80 | 0 | 3 | 2 | 5 | 5 |
|  | 20 | 0 | 0 | 0 | 5 | 5 |

TEST EXAMPLE 4

Plastic trays (35 cm × 25 cm × 15 cm) were filled with upland field soil, and the seeds of soybean, cotton, corn, wheat as well as cocklebur, velvetleaf, tall morning-glory, prickly sida, pineappleweed and wild buckwheat were sowed therein. A designed amount of the test compound formulated into an emulsifiable concentrate and dispersed in water was sprayed over the top by means of a small hand sprayer at a spray volume of 10 liters per are. After the spraying, the test plants were grown in a greenhouse for 20 days, and phytotoxicity and herbicidal activity were examined. The results are shown in Table 5.

TABLE 5

| Compound No. | Dosage (weight of active ingredient, g/are) | Phytotoxicity Soybean | Cotton | Corn | Wheat | Herbicidal activity Cocklebur | Velvetleaf | Tall morningglory | Prickly sida | Pineappleweed | Wild buckwheat |
| --- | --- | --- | --- | --- | --- | --- | --- | --- | --- | --- | --- |
| 11 | 40 | 1 | — | 1 | 0 | 5 | 5 | 5 | 5 | 5 | 5 |
|    | 20 | 0 | 0 | 0 | 0 | 4 | 5 | 4 | 5 | 5 | 4 |
| 16 | 40 | 1 | — | 0 | 0 | 5 | 5 | 5 | 5 | 5 | 5 |
|    | 20 | 0 | 1 | 0 | 0 | 5 | 5 | 5 | 5 | 5 | 5 |
| 20 | 40 | 0 | — | 1 | 0 | 5 | 5 | 5 | 5 | 5 | 4 |
|    | 20 | 0 | 1 | 0 | 0 | 4 | 5 | 5 | 5 | 5 | 4 |

TEST EXAMPLE 5

Wagner's pots (1/5000 are) were filled with paddy field soil and the seeds of barnyardgrass, hardstem bulrush and broad-leaved weeds (e.g. false pimpernel, monochoria, toothcup) were sowed therein at 3 cm depth, and water was poured until the depth of water became 4 cm. Seedlings of rice plants at 3-leaf stage as well as tubers of arrowhead were transplanted therein, and the test plants were grown for 5 days in a greenhouse. At the time of germination, a designed amount of the test compound formulated into an emulsifiable concentrate was applied to the pots by perfusion. The test plants were grown for further 20 days, and herbicidal activity and phytotoxicity were examined. The results are shown in Table 6.

TABLE 6

| Compound No. | Dosage (weight of active ingredient, g/are) | Phytotoxicity Rice plant | Herbicidal activity Barnyardgrass | Broadleaved weed | Hardstem bulrush | Arrowhead |
| --- | --- | --- | --- | --- | --- | --- |
| 1 | 5 | 1 | 5 | 5 | 4 | 5 |
|   | 2.5 | 0 | 3 | 5 | 3 | 3 |
| 3 | 5 | 1 | 5 | 5 | 4 | 5 |
|   | 2.5 | 1 | 5 | 5 | 4 | 3 |
| 6 | 5 | 1 | 5 | 5 | 4 | 5 |
|   | 2.5 | 1 | 5 | 5 | 4 | 4 |
| 7 | 5 | 1 | 5 | 5 | 5 | 5 |
|   | 2.5 | 0 | 5 | 5 | 4 | 4 |
| 8 | 5 | 1 | 5 | 5 | 4 | 5 |
|   | 2.5 | 0 | 5 | 5 | 3 | 4 |
| 9 | 5 | 1 | 5 | 5 | 4 | 5 |
|   | 2.5 | 0 | 5 | 5 | 3 | 4 |
| 10 | 5 | 1 | 5 | 5 | 5 | 5 |
|    | 2.5 | 1 | 5 | 5 | 4 | 5 |
| 11 | 5 | 1 | 5 | 5 | 5 | 5 |
|    | 2.5 | 1 | 5 | 5 | 4 | 5 |
| 12 | 5 | 1 | 5 | 5 | 5 | 5 |
|    | 2.5 | 0 | 5 | 5 | 4 | 4 |
| 14 | 5 | 1 | 5 | 5 | 4 | 5 |
|    | 2.5 | 0 | 4 | 5 | 3 | 4 |
| 16 | 5 | 1 | 5 | 5 | 4 | 5 |
|    | 2.5 | 0 | 5 | 5 | 3 | 4 |
| 19 | 5 | 1 | 5 | 5 | 4 | 5 |
|    | 2.5 | 0 | 4 | 5 | 4 | 5 |
| 21 | 5 | — | 5 | 5 | — | 5 |
|    | 2.5 | 1 | 4 | 5 | — | 5 |
| 23 | 5 | 1 | 5 | 5 | — | 5 |
|    | 2.5 | 1 | 4 | 5 | — | 4 |
| 25 | 5 | 1 | 4 | 5 | 4 | 5 |
|    | 2.5 | 0 | 3 | 5 | 4 | 3 |
| 26 | 10 | 1 | 5 | 5 | 4 | 5 |
|    | 5 | 0 | 3 | 5 | 3 | 3 |
| 27 | 5 | 1 | 5 | 5 | 5 | 5 |
|    | 2.5 | 0 | 5 | 5 | 5 | 5 |
| 28 | 5 | — | 5 | 5 | 4 | 5 |
|    | 2.5 | 0 | 5 | 5 | 3 | 4 |
| 29 | 5 | 1 | 5 | 5 | 4 | 5 |
|    | 2.5 | 0 | 5 | 5 | 3 | 3 |
| 31 | 2.5 | 1 | 5 | 5 | 5 | 5 |
|    | 1.25 | 1 | 5 | 5 | 4 | 5 |
| 32 | 2.5 | 1 | 5 | 5 | 4 | 5 |
|    | 1.25 | 1 | 5 | 5 | 3 | 4 |
| 33 | 5 | 1 | 5 | 5 | 5 | 5 |
|    | 2.5 | 0 | 5 | 5 | 4 | 4 |
| 37 | 5 | — | 5 | 5 | 4 | 5 |
|    | 2.5 | 1 | 5 | 5 | 3 | 4 |
| 39 | 10 | 1 | 5 | 5 | 4 | 5 |
|    | 5 | 1 | 5 | 5 | 3 | 3 |
| 40 | 5 | 1 | 5 | 5 | 3 | 5 |
|    | 2.5 | 0 | 5 | 5 | 2 | 3 |
| 42 | 5 | 1 | 5 | 5 | 5 | 4 |
|    | 2.5 | 0 | 5 | 5 | 3 | 4 |
| 43 | 2.5 | 1 | 5 | 5 | 5 | 4 |
|    | 1.25 | 0 | 5 | 5 | 4 | 2 |
| 44 | 5 | 1 | 5 | 5 | 3 | 4 |
|    | 2.5 | 0 | 5 | 5 | 4 | 4 |
| 45 | 2.5 | 1 | 5 | 5 | 4 | 4 |
|    | 1.25 | 1 | 5 | 5 | 3 | 3 |
| 46 | 2.5 | 1 | 5 | 5 | 4 | 4 |
|    | 1.25 | 0 | 5 | 5 | 3 | 3 |
| 47 | 5 | 1 | 5 | 5 | 3 | 4 |
|    | 2.5 | 1 | 5 | 5 | 3 | 3 |
| 49 | 2.5 | 1 | 5 | 5 | — | 5 |
|    | 1.25 | 1 | 5 | 5 | — | 3 |
| 50 | 5 | 1 | 5 | 5 | 4 | 5 |
|    | 2.5 | 0 | 5 | 5 | 3 | 3 |
| 52 | 5 | 1 | 5 | 5 | 4 | 5 |
|    | 2.5 | 0 | 4 | 5 | 3 | 4 |
| 53 | 5 | 0 | 5 | 5 | 5 | 5 |
|    | 2.5 | 0 | 5 | 5 | 3 | 4 |
| 55 | 5 | 1 | 5 | 5 | 3 | 5 |
|    | 2.5 | 0 | 5 | 5 | 2 | 4 |
| 56 | 2.5 | 1 | 5 | 5 | 4 | 5 |
|    | 1.25 | 1 | 4 | 5 | 3 | 4 |
| 57 | 5 | 1 | 5 | 5 | 4 | 4 |
|    | 2.5 | 1 | 5 | 5 | 3 | 4 |
| 59 | 2.5 | 1 | 5 | 5 | 3 | 5 |
|    | 1.25 | 1 | 5 | 5 | 2 | 4 |
| 60 | 5 | 1 | 5 | 5 | 3 | 4 |
|    | 2.5 | 0 | 5 | 5 | 1 | 3 |
| 62 | 5 | 0 | 5 | 5 | 3 | 5 |
|    | 2.5 | 0 | 4 | 5 | 2 | 4 |
| 63 | 5 | 0 | 5 | 5 | — | 5 |
|    | 2.5 | 0 | 4 | 5 | — | 4 |
| 64 | 5 | 1 | 5 | 5 | — | 5 |
|    | 2.5 | 0 | 5 | 5 | — | 5 |
| 65 | 10 | 1 | 5 | 5 | 3 | 5 |
|    | 5 | 0 | 5 | 5 | 2 | 4 |
| 66 | 10 | 0 | 5 | 5 | — | 4 |
|    | 5 | 0 | 5 | 5 | — | 3 |
| 67 | 10 | 1 | 5 | 5 | 4 | 4 |
|    | 5 | 0 | 5 | 5 | 2 | 3 |
| 68 | 10 | — | 5 | 5 | — | 4 |
|    | 5 | 1 | 4 | 5 | — | 3 |
| 69 | 10 | 1 | 5 | 5 | — | 4 |
|    | 5 | 1 | 5 | 5 | — | 3 |

TABLE 6-continued

| Compound No. | Dosage (weight of active ingredient, g/are) | Phytotoxicity Rice plant | Barnyardgrass | Broadleaved weed | Hardstem bulrush | Arrowhead |
|---|---|---|---|---|---|---|
| 70 | 10 | 1 | 5 | 5 | — | 5 |
|  | 5 | 1 | 5 | 5 | — | 3 |
| 71 | 5 | 1 | 5 | 5 | — | 5 |
|  | 2.5 | 0 | 5 | 5 | — | 4 |
| 72 | 5 | 0 | 5 | 5 | 4 | 5 |
|  | 2.5 | 0 | 5 | 5 | 3 | 5 |
| 73 | 5 | 1 | 5 | 5 | 3 | 4 |
|  | 2.5 | 1 | 5 | 5 | 2 | 3 |
| 74 | 10 | 1 | 5 | 5 | — | 4 |
|  | 5 | 1 | 5 | 5 | — | 3 |
| 75 | 10 | 1 | 5 | 5 | — | 4 |
|  | 5 | 0 | 4 | 5 | — | 2 |
| 76 | 10 | 1 | 5 | 5 | — | 3 |
|  | 5 | 0 | 5 | 5 | — | 2 |
| 77 | 10 | 0 | 5 | 5 | — | 4 |
|  | 5 | 0 | 4 | 5 | — | 3 |
| 78 | 10 | 1 | — | 5 | 5 | 4 |
|  | 5 | 0 | — | 4 | 4 | 3 |
| 79 | 10 | 0 | 5 | 5 | — | 4 |
|  | 5 | 0 | 5 | 5 | — | 2 |
| 80 | 10 | 0 | 5 | 5 | — | 3 |
|  | 5 | 0 | 5 | 5 | — | 2 |
| 81 | 10 | — | 5 | 5 | — | 5 |
|  | 5 | 1 | 5 | 5 | — | 4 |
| 82 | 10 | 1 | 5 | 5 | — | — |
|  | 5 | 0 | 5 | 5 | — | — |
| 83 | 10 | 0 | 5 | 5 | 3 | 4 |
| 84 | 10 | 0 | 5 | 5 | — | — |
| 85 | 10 | 0 | 5 | 5 | — | — |
| 86 | 10 | 0 | 5 | 5 | 3 | 5 |
| 87 | 10 | 0 | 5 | 5 | — | — |
| 88 | 10 | 1 | 5 | 5 | 3 | 5 |
| 89 | 2.5 | 0 | 5 | 5 | — | 5 |
|  | 1.25 | 0 | 5 | 5 | — | 4 |
| 91 | 10 | 1 | 5 | 5 | 3 | 4 |
| 92 | 10 | 1 | 5 | 5 | — | 5 |
|  | 5 | 0 | 5 | 5 | — | 4 |
| 93 | 10 | 0 | 5 | 5 | — | 4 |
|  | 5 | 0 | 4 | 5 | — | 2 |
| 94 | 2.5 | 1 | 5 | 5 | 4 | 5 |
|  | 1.25 | 0 | 4 | 5 | 3 | 5 |
| 95 | 5 | 1 | 5 | 5 | 5 | 5 |
|  | 2.5 | 0 | 4 | 5 | 3 | 5 |
| 96 | 2.5 | 0 | 5 | 5 | — | 5 |
|  | 1.25 | 0 | 5 | 5 | — | 3 |
| 97 | 2.5 | 1 | 5 | 5 | — | 5 |
|  | 1.25 | 0 | 4 | 5 | — | 3 |
| 98 | 2.5 | 1 | 5 | 5 | 4 | 5 |
|  | 1.25 | 1 | 5 | 5 | 2 | 4 |
| 99 | 5 | 0 | 5 | 5 | 3 | 4 |
|  | 2.5 | 0 | 5 | 5 | — | — |
| 100 | 5 | 0 | 5 | 5 | 4 | 5 |
|  | 2.5 | 0 | 5 | 5 | 2 | 5 |
| 101 | 10 | 1 | 5 | 5 | 4 | 5 |
|  | 5 | 0 | 5 | 5 | — | 4 |
| 105 | 10 | 0 | 5 | 5 | 2 | 5 |
| 106 | 10 | 2 | 5 | 5 | 4 | 3 |
| 107 | 2.5 | 1 | 5 | 5 | 4 | 4 |
|  | 1.25 | 1 | 4 | 5 | 4 | 3 |
| 108 | 10 | 0 | 5 | 5 | 5 | 2 |
| 109 | 10 | 2 | 5 | 5 | 4 | 4 |
|  | 2.5 | 1 | 5 | 5 | 4 | 3 |
| 110 | 2.5 | 2 | 5 | 5 | 4 | 5 |
|  | 1.25 | 0 | 5 | 5 | 3 | 3 |
| 111 | 2.5 | 0 | 5 | 5 | 5 | 4 |
| 112 | 10 | 1 | 5 | 5 | 4 | 5 |
|  | 2.5 | 0 | 5 | 5 | 4 | 4 |
| 113 | 10 | 0 | 5 | 5 | 4 | 5 |
|  | 2.5 | 0 | 5 | 5 | 3 | 4 |
| 114 | 2.5 | 1 | 5 | 5 | 5 | 5 |
|  | 1.25 | 0 | 5 | 5 | 5 | 3 |
| 115 | 2.5 | 1 | 5 | 5 | 4 | 4 |
|  | 1.25 | 0 | 5 | 5 | 3 | 3 |
| 116 | 2.5 | 0 | 5 | 5 | 5 | 3 |
| 117 | 2.5 | 2 | 5 | 5 | 5 | 5 |
|  | 1.25 | 1 | 5 | 5 | 4 | 5 |
| 118 | 2.5 | 2 | 5 | 5 | 5 | 5 |
|  | 1.25 | 0 | 5 | 5 | 5 | 4 |
| 119 | 2.5 | 1 | 5 | 5 | 5 | 5 |
|  | 1.25 | 0 | 5 | 5 | 4 | 3 |
| 121 | 2.5 | 0 | 5 | 5 | 4 | 5 |
|  | 1.25 | 0 | 5 | 5 | 3 | 4 |
| 122 | 2.5 | 0 | 5 | 5 | 3 | 4 |
| 123 | 2.5 | 0 | 5 | 5 | 5 | 4 |
| 124 | 40 | 0 | 5 | 5 | 5 | 5 |
|  | 10 | 0 | 5 | 5 | 4 | 5 |
| 125 | 10 | 1 | 5 | 5 | 4 | 3 |
| 126 | 10 | 1 | 5 | 5 | 5 | 4 |
|  | 2.5 | 0 | 5 | 5 | 4 | 3 |
| 127 | 10 | 1 | 5 | 5 | 5 | 5 |
|  | 2.5 | 0 | 5 | 5 | 4 | 4 |
| 132 | 40 | 2 | 5 | 5 | 4 | 5 |
|  | 10 | 1 | 5 | 5 | 3 | 3 |
| 134 | 40 | 2 | 5 | 5 | 5 | 5 |
|  | 10 | 1 | 5 | 5 | 4 | 4 |
| 135 | 10 | 2 | 5 | 5 | 5 | 5 |
|  | 2.5 | 1 | 5 | 5 | 4 | 5 |
| 136 | 2.5 | 0 | 5 | 5 | 5 | 4 |
|  | 1.25 | 0 | 5 | 5 | 5 | 4 |
| 138 | 10 | 1 | 5 | 5 | 5 | 5 |
|  | 2.5 | 0 | 5 | 5 | 4 | 4 |
| 139 | 10 | 2 | 5 | 5 | 4 | 5 |
| 140 | 10 | 1 | 5 | 5 | 4 | 5 |
|  | 2.5 | 0 | 5 | 5 | 3 | 5 |
| 142 | 10 | 0 | 5 | 5 | 4 | 4 |
|  | 2.5 | 0 | 5 | 5 | 4 | 4 |
| 143 | 10 | 1 | 5 | 5 | 4 | 5 |
|  | 2.5 | 0 | 5 | 5 | 3 | 4 |
| 144 | 10 | 1 | 5 | 5 | 4 | 5 |
|  | 2.5 | 0 | 5 | 5 | 4 | 4 |
| Chlormethoxynil* | 5 | 1 | 5 | 5 | 4 | 3 |
|  | 2.5 | 0 | 4 | 5 | 2 | 2 |

Note:
*Commercially available herbicide having the following formula:

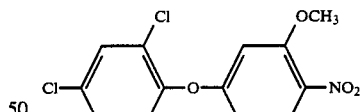

TEST EXAMPLE 6

Plastic trays (35 cm × 25 cm × 15 cm) were filled with upland field soil, and the seeds of soybean, cocklebur, common ragweed, velvetleaf, prickly sida, sicklepod, tall morningglory, black nightshade, jimsonweed and redroot pigweed were sowed therein. A designed amount of the test compound formulated into an emulsifiable concentrate and dispersed in water was sprayed to the soil surface at a spray volume of 10 liters per are. After the spraying, the test plants were grown for 20 days in outdoors (atmospheric temperature: maximum, 30° C.; minimum, 12° C.; total rainfall: 22 mm), and herbicidal activity and phytotoxicity were examined. The results are shown in Table 7.

TABLE 7

| Compound No. | Dosage (weight of active ingredient, g/are) | Phyto-toxicity Soybean | Herbicidal activity | | | | | | | | |
|---|---|---|---|---|---|---|---|---|---|---|---|
| | | | Cock-lebur | Common rag-weed | Velvet-leaf | Prickly sida | Sickle-pod | Tall morning-glory | Black night-shade | Jimson-weed | Redroot pigweed |
| 5 | 10 | 1 | 4 | 5 | 5 | 5 | 5 | 5 | 5 | 5 | 5 |
|  | 5 | 1 | 2 | 5 | 5 | 5 | 4 | 4 | 5 | 5 | 5 |
| 10 | 5 | 1 | 5 | 5 | 5 | 5 | 4 | 4 | 5 | 5 | 5 |
|  | 2.5 | 0 | 3 | 4 | 5 | 5 | 3 | 2 | 5 | 5 | 5 |
| 11 | 10 | 0 | 5 | 5 | 5 | 5 | 4 | 5 | 5 | 5 | 5 |
|  | 5 | 0 | 3 | 5 | 5 | 5 | 2 | 4 | 5 | 5 | 5 |
| 13 | 10 | 1 | 4 | 5 | 5 | 5 | 4 | 5 | 5 | 5 | 5 |
|  | 5 | 0 | 3 | 5 | 5 | 5 | 3 | 4 | 5 | 5 | 5 |
| 14 | 5 | 1 | 4 | 5 | 5 | 5 | 4 | 5 | 5 | 5 | 5 |
|  | 2.5 | 1 | 3 | 5 | 5 | 5 | 3 | 3 | 5 | 5 | 5 |
| 16 | 10 | 1 | 4 | 5 | 5 | 5 | 4 | 5 | 5 | 5 | 5 |
|  | 5 | 1 | 3 | 5 | 5 | 5 | 3 | 4 | 5 | 5 | 5 |
| 17 | 5 | 1 | 4 | 5 | 5 | 5 | 5 | 5 | 5 | 5 | 5 |
|  | 2.5 | 1 | 4 | 5 | 5 | 5 | 4 | 3 | 5 | 5 | 5 |
| 18 | 10 | 0 | 5 | 5 | 5 | 5 | 4 | 5 | 5 | 5 | 5 |
|  | 5 | 0 | 3 | 4 | 5 | 5 | 2 | 4 | 5 | 5 | 5 |
| 20 | 10 | 0 | 4 | 5 | 5 | 5 | 5 | 5 | 5 | 5 | 5 |
|  | 5 | 0 | 2 | 5 | 5 | 5 | 4 | 4 | 5 | 5 | 5 |
| 21 | 10 | 0 | 4 | 5 | 5 | 5 | 4 | 5 | 5 | 5 | 5 |
|  | 5 | 0 | 3 | 5 | 5 | 5 | 3 | 4 | 5 | 5 | 5 |
| 37 | 10 | 1 | 5 | 5 | 5 | 5 | 4 | 5 | 5 | 5 | 5 |
|  | 5 | 0 | 3 | 5 | 5 | 5 | 3 | 5 | 5 | 5 | 5 |
| 39 | 10 | — | 4 | 5 | 5 | 5 | 4 | 5 | 5 | 5 | 5 |
|  | 5 | 1 | 3 | 5 | 5 | 5 | 3 | 4 | 5 | 5 | 5 |
| 40 | 10 | 1 | 4 | 5 | 5 | 5 | 5 | 5 | 5 | 5 | 5 |
|  | 5 | 0 | 2 | 5 | 5 | 5 | 4 | 4 | 5 | 5 | 5 |
| 43 | 10 | 1 | 4 | 5 | 5 | 5 | 4 | 4 | 5 | 5 | 5 |
|  | 5 | 0 | 2 | 5 | 5 | 4 | 2 | 3 | 5 | 5 | 5 |
| 44 | 10 | 1 | 5 | 5 | 5 | 5 | 3 | 5 | 5 | 5 | 5 |
|  | 5 | 0 | 3 | 5 | 5 | 5 | 2 | 4 | 5 | 5 | 5 |
| 45 | 10 | — | 5 | 5 | 5 | 5 | 5 | 5 | 5 | 5 | 5 |
|  | 5 | 1 | 4 | 5 | 5 | 5 | 4 | 4 | 5 | 5 | 5 |
| 49 | 5 | — | 4 | 5 | 5 | 5 | 5 | 5 | 5 | 5 | 5 |
|  | 2.5 | 1 | 2 | 5 | 5 | 4 | 3 | 3 | 5 | 5 | 5 |
| 52 | 5 | — | 4 | 5 | 5 | 5 | 5 | 5 | 5 | 5 | 5 |
|  | 2.5 | 1 | 2 | 5 | 5 | 5 | 3 | 3 | 5 | 5 | 5 |
| 53 | 10 | 1 | 2 | 5 | 5 | 5 | 2 | 5 | 5 | 5 | 5 |
|  | 5 | 0 | 1 | 5 | 5 | 4 | 1 | 4 | 5 | 5 | 5 |
| 56 | 5 | 1 | 5 | 5 | 5 | 5 | 4 | 5 | 5 | 5 | 5 |
|  | 2.5 | 1 | 4 | 5 | 5 | 5 | 2 | 4 | 5 | 5 | 5 |
| 58 | 5 | 1 | 2 | 5 | 5 | 4 | 3 | 4 | 5 | 5 | 5 |
|  | 2.5 | 1 | 2 | 5 | 5 | 3 | 2 | 3 | 5 | 5 | 5 |
| 63 | 10 | 1 | 5 | 5 | 5 | 5 | 5 | 5 | 5 | 5 | 5 |
|  | 5 | 0 | 2 | 5 | 5 | 5 | 3 | 3 | 5 | 5 | 5 |
| 64 | 10 | 1 | 5 | 5 | 5 | 5 | 5 | 5 | 5 | 5 | 5 |
|  | 5 | 0 | 4 | 5 | 5 | 5 | 3 | 3 | 5 | 5 | 5 |
| 68 | 10 | 1 | 4 | 5 | 5 | 5 | 3 | 5 | 5 | 5 | 5 |
|  | 5 | 1 | 2 | 5 | 5 | 5 | 1 | 4 | 5 | 5 | 5 |
| 73 | 5 | 1 | 4 | 5 | 5 | 5 | 4 | 5 | 5 | 5 | 5 |
|  | 2.5 | 0 | 3 | 5 | 5 | 5 | 3 | 3 | 5 | 5 | 5 |
| 75 | 10 | 1 | 4 | 5 | 5 | 5 | 4 | 5 | 5 | 5 | 5 |
|  | 5 | 1 | 3 | 5 | 5 | 5 | 2 | 4 | 5 | 5 | 5 |
| 76 | 10 | — | 3 | 5 | 5 | 5 | 5 | 5 | 5 | 5 | 5 |
|  | 5 | 1 | 1 | 5 | 5 | 5 | 3 | 4 | 5 | 5 | 5 |
| 82 | 10 | 1 | 3 | 5 | 5 | 5 | 4 | 5 | 5 | 5 | 5 |
|  | 5 | 1 | 1 | 5 | 5 | 5 | 2 | 3 | 5 | 5 | 4 |
| 85 | 10 | 1 | 3 | 5 | 5 | 5 | 4 | 5 | 5 | 5 | 5 |
|  | 5 | 1 | 2 | 5 | 5 | 4 | 3 | 3 | 5 | 5 | 5 |
| 107 | 10 | 1 | 4 | 5 | 5 | 5 | 5 | 5 | 5 | 5 | 5 |
|  | 5 | 1 | 2 | 5 | 5 | 5 | 4 | 5 | 5 | 5 | 5 |
| 108 | 10 | 1 | 5 | 5 | 5 | 5 | 5 | 5 | 5 | 5 | 5 |
|  | 5 | 0 | 4 | 5 | 4 | 5 | 4 | 4 | 5 | 4 | 5 |
| 114 | 5 | 1 | 4 | 5 | 5 | 5 | 4 | 5 | 5 | 5 | 5 |
|  | 2.5 | 1 | 2 | 5 | 5 | 5 | 4 | 5 | 5 | 5 | 5 |
| 115 | 5 | 1 | 4 | 5 | 5 | 5 | 4 | 5 | 5 | 5 | 5 |
|  | 2.5 | 0 | 3 | 5 | 5 | 5 | 4 | 5 | 5 | 5 | 5 |
| 117 | 5 | 1 | 4 | 5 | 5 | 5 | 5 | 5 | 5 | 5 | 5 |
|  | 2.5 | 0 | 3 | 5 | 5 | 5 | 4 | 5 | 5 | 5 | 5 |
| Oxy-fluoro- | 10 | 3 | 3 | 5 | 5 | 5 | 2 | 5 | 5 | 5 | 5 |
|  | 5 | 1 | 1 | 5 | 5 | 5 | 1 | 3 | 5 | 5 | 5 |

TABLE 7-continued

| Compound No. | Dosage (weight of active ingredient, g/are) | Phyto- toxicity Soybean | Herbicidal activity | | | | | | | |
|---|---|---|---|---|---|---|---|---|---|---|
| | | | Cock- lebur | Common rag- weed | Velvet- leaf | Prickly sida | Sickle- pod | Tall morning- glory | Black night- shade | Jimson- weed | Redroot pigweed |
| fen* | | | | | | | | | | | |

Note:
*Commercially available herbicide having the following formula:

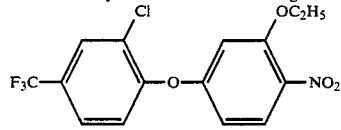

What is claimed is:

1. A diphenyl sulfone compound of the formula:

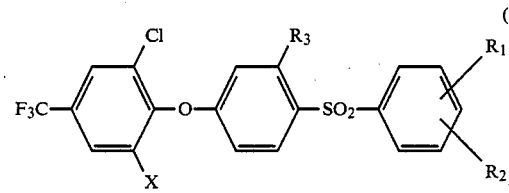

wherein $R_1$ and $R_2$ are, same or different, each a hydrogen atom, a halogen atom, a lower alkyl group, a lower alkoxy group, a lower alkenyloxy group, a lower alkynyloxy group, a phenoxy group, a lower alkylthio group, a lower alkylsulfonyl group or a lower alkoxycarbonyl(lower)alkoxy group, $R_3$ is a hydroxyl group, a lower alkenyloxy group, a lower alkynyloxy group, a halo(lower)alkoxy group, a dihalo(lower)alkoxy group, a lower alkoxy(lower)alkoxy group, a cyano(lower)alkoxy group, a lower alkoxycyano(lower)alkoxy group, a hydroxy(lower)alkoxy group, a lower alkylcarbonyloxy group, a lower alkoxycarbonyl group, a lower alkylthio(lower)alkoxy group, a lower alkenyloxy(lower)alkoxy group, a di(lower)alkylamino(lower)alkoxy group, a hydroxyimino(lower)alkoxy group, a lower alkoxyimino(lower)alkoxy group, a lower alkylsulfonyloxy group, a lower alkoxycarbonyloxy group, a di(lower)alkoxyphosphinyloxy group, an oxotetrahydrofuranyloxy group, a tetrahydropyranyloxy group, a lower alkyl-1,3-oxolanyl(lower)alkoxy group or a group of the formula: —O—A—COR$_4$ (in which A is lower alkylene, lower alkenylene, lower alkyleneoxy, halo(lower)alkylene or lower alkoxy(lower)alkylene and R$_4$ is hydroxyl, lower alkyl, halo(lower)alkyl, lower alkoxy, lower alkenyloxy, lower alkynyloxy, halo(-lower)alkoxy, lower alkoxy(lower)alkoxy, cyano(-lower)alkoxy, lower alkoxycarbonyl(lower)alkoxy, di(-lower)alkylamino, N-(α-lower alkyl(lower)alkylidene)aminoxy or lower alkylthio) and X is a hydrogen atom or a halogen atom.

2. The diphenyl sulfone compound according to claim 1, wherein $R_1$ and $R_2$ are, same or different, each a hydrogen atom, a fluorine atom, a chlorine atom, a bromine atom, a $C_1$-$C_2$ alkyl group, a $C_1$-$C_2$ alkoxy group, a propenyloxy group, a propynyloxy group, a phenoxy group, a methylthio group, a methylsulfonyl group or a ($C_1$-$C_2$)alkoxycarbonyl($C_1$-$C_2$)alkoxy group, $R_3$ is a hydroxyl group, a propenyloxy group, a propynyloxy group, a chloroethoxy group, a difluoromethoxy group, a $C_1$-$C_2$ alkoxy($C_1$-$C_2$)alkoxy group, a cyanomethoxy group, a cyanomethoxymethoxy group, a hydroxyethoxy group, an ethoxycarbonyl group, a $C_1$-$C_2$ alkylthio($C_1$-$C_2$)alkoxy group, an ethenyloxyethoxy group, an N,N-di($C_1$-$C_2$)alkylaminoethoxy group, a hydroxyiminoethoxy group, a methoxyiminoethoxy group, a methylsulfonyloxy group, a methoxycarbonyloxy group, a diethoxyphosphinyloxy group, an oxotetrahydrofuranyl group, a tetrahydropyranyloxy group, a methyl-1,3-oxolanyl($C_1$-$C_2$)alkoxy group or a methylcarbonyloxy group, A is a $C_1$-$C_2$ alkylene group, a propenylene group, an ethyleneoxy group, a fluoromethylene group or a methoxymethylene group and R$_4$ is a $C_1$-$C_4$ alkyl group, a chloromethyl group, a hydroxyl group, a $C_1$-$C_5$ alkoxy group, a chloroethoxy group, a propenyloxy group, an ethoxycarbonylethoxy group, an α-methylethylideneaminoxy group, an N,N-dimethylamino group, a cyanomethoxy group, a methoxyethoxy group, an ethylthio group or a propynyloxy group.

3. The diphenyl sulfone compound according to claim 1, wherein $R_1$ and $R_2$ are, same or different, each a hydrogen atom, a methyl group, an ethyl group, a fluorine atom, a chlorine atom, a bromine atom, a methoxy group or an ethoxy group, $R_3$ is a chloroethyloxy group, a methoxymethoxy group, a cyanomethoxy group, a methoxycyanomethoxy group, a hydroxyethoxy group, a methylcarbonylmethoxy group, an α-(methylcarbonyl)ethoxy group, a methylthiomethyl group, a methylthiomethoxy group, a methoxyiminopropoxy group, a diethoxyphosphinyloxy group, an oxotetrahydrofuranyloxy group, a methoxycarbonylmethoxy group, an ethoxycarbonylmethyl group, an α-(methoxycarbonyl)ethoxy group, a methoxy(methoxycarbonyl)methoxy group, an α-(ethoxycarbonyl)ethoxy group, an ethylthiocarbonylmethoxy group, a propinyloxycarbonylmethoxy group, a 2-methyl-1,3-oxolan-2-ylmethoxy group, an α-(2-methyl-1,3-oxolan-2-yl)ethoxy group, a β-(methylcarbonyloxy)ethoxy group, a β-(ethoxycarbonyloxy)ethoxy group or a dimethylaminocarbonylmethoxy group and X is a hydrogen atom or a chlorine atom.

4. The diphenyl sulfone compound according to claim 1, i.e. 4-(2-chloro-4trifluoromethylphenoxy)-2-cyanomethoxy-4'-methyldiphenyl sulfone.

5. The dipheny sulfone compound according to claim 1, i.e. 4-(2-chloro-4-trifluoromethylphenoxy)-2-cyanomethoxy-4'-chlorodiphenyl sulfone.

6. The diphenyl sulfone compound according to claim 1, i.e. 4-(2-chloro-4-trifluoromethylphenoxy)-2-methoxycarbonylmethoxydiphenyl sulfone.

7. The diphenyl sulfone compound according to claim 1, i.e. 4-(2-chloro-4-trifluoromethylphenoxy)-2-methoxycarbonylmethoxy-4'-methyldiphenyl sulfone.

8. The diphenyl sulfone compound according to claim 1, i.e. 4-(2-chloro-4-trifluoromethylphenoxy)-2-methoxycarbonylmethoxy-4'-chlorodiphenyl sulfone.

9. The diphenyl sulfone compound according to claim 1, i.e. 4-(2-chloro-4-trifluoromethylphenoxy)-2-ethoxycarbonylmethoxy-4'-methyldiphenyl sulfone.

10. The diphenyl sulfone compound according to claim 1, i.e. 4-(2-chloro-4-trifluoromethylphenoxy)-2-methoxycarbonylmethoxy-4'-fluorodiphenyl sulfone.

11. The diphenyl sulfone compound according to claim 1, i.e. 4-(2-chloro-4trifloromethylphenoxy)-2-methoxy(methoxycarbonyl)methoxydiphenyl sulfone.

12. The diphenyl sulfone compound according to claim 1, i.e. 4-(2-chloro-4-trifluoromethylphenoxy)-2-[methoxy(methoxycarbonyl)methoxy]-4'-chlorodiphenyl sulfone.

13. The diphenyl sulfone compound according to claim 1, i.e. 4-(2-chloro-4-trifluoromethylphenoxy)-2-(1-acetylethoxy)-4'-chlorodiphenyl sulfone.

14. The diphenyl sulfone compound according to claim 1, i.e. 4-(2-chloro-4-trifluoromethylphenoxy)-2-(1-acetylethoxy)-4'-fluorodiphenyl sulfone.

15. A herbicidal composition which comprises a herbicidally effective amount of the diphenyl sulfone compound (I) claimed in claim 1 and an inert carrier or diluent.

16. A method for controlling weeds which comprises applying a herbicidally effective amount of the diphenyl sulfone compound (I) claimed in claim 1 to the area where the weeds grow or will grow.

17. The method according to claim 16, wherein the area is a field of rice, corn, soybean or wheat.

* * * * *